United States Patent [19]
Seidel et al.

[11] Patent Number: 5,187,276
[45] Date of Patent: Feb. 16, 1993

[54] 2-PYRIMIDINYL-1-PIPERAZINE DERIVATIVES

[75] Inventors: Peter-Rudolf Seidel, Cologne; Harald Horstmann, Wuppertal; Jorg Traber, Lohmar; Wolfgang Dompert, Roesrath-Forsbach; Thomas Glaser, Cologne; Teunis Thurman, Overath, all of Fed. Rep. of Germany

[73] Assignee: Troponwerke GmbH & Co. KG., Cologne, Fed. Rep. of Germany

[21] Appl. No.: 619,270

[22] Filed: Nov. 28, 1990

Related U.S. Application Data

[62] Division of Ser. No. 482,580, Feb. 21, 1990, Pat. No. 4,988,809, which is a division of Ser. No. 247,813, Sep. 22, 1988, Pat. No. 4,937,343, which is a division of Ser. No. 838,238, Mar. 10, 1986, Pat. No. 4,818,756, which is a division of Ser. No. 617,858, Jun. 6, 1984, abandoned.

[30] Foreign Application Priority Data

Jun. 18, 1983 [DE] Fed. Rep. of Germany ....... 3321969

[51] Int. Cl.⁵ ............................................. C07D 403/04
[52] U.S. Cl. ...................................... 544/295; 544/12; 544/49; 544/94; 544/116; 544/121; 544/231; 544/284; 544/285; 548/123; 548/210
[58] Field of Search .......................................... 544/295

[56] References Cited

U.S. PATENT DOCUMENTS 4,423,049 12/1983 Temple, Jr. ........................ 514/252

Primary Examiner—C. Warren Ivy
Assistant Examiner—James H. Turnipseed
Attorney, Agent, or Firm—Sprung Horn Kramer & Woods

[57] ABSTRACT

The invention relates to substituted 2-pyrimidinyl-1-piperazine derivatives defined herein by formula (I), processes for their manufacture, compositions containing said substituted 2-pyrimidinyl-1-piperazine derivatives as active materials and the use of said compounds and compositions as agents effecting the central nervous system. Also included in the invention are intermediates of formula (VIII) for making the active formula (I) compounds.

1 Claim, No Drawings

2-PYRIMIDINYL-1-PIPERAZINE DERIVATIVES

This is a division of application Ser. No. 07/482,580, filed Feb. 21, 1990, now U.S. Pat. No. 4,988,809, which is a division of Ser. No. 07/247,813 filed Sep. 22, 1988, now U.S. Pat. No. 4,937,343.

The present invention relates to new substituted 2-pyrimidinyl-1-piperazine derivatives of the formula (I), to processes for their preparation and to medicaments containing them, in particular agents affecting the central nervous system.

It has been found that the new substituted 2-pyrimidinyl-1-piperazine derivatives of the formula (I)

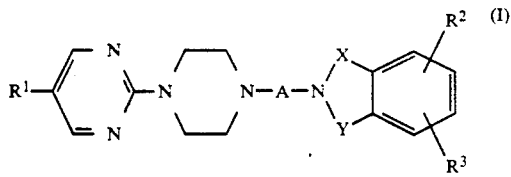

in which
A represents an optionally substituted alkylene radical,
$R^1$ denotes hydrogen, optionally substituted alkyl, aralkyl, halogen, hydroxyl, nitro, cyano, optionally substituted alkoxy, optionally substituted aryl or heteroaryl, alkylamino or arylamino, alkylmercapto or acylamino,
$R^2$ and $R^3$, which can be identical or different, represent hydrogen, optionally substituted alkyl, optionally substituted aryl, aralkyl, cycloalkyl, optionally substituted alkoxy, phenoxy, halogen, hydroxyl, alkylamino, arylamino, nitro, alkylmercapto, phenylmercapto, cyano, carboxyl, alkoxycarbonyl, optionally substituted carbamoyl or optionally substituted sulphamoyl,
X denotes carbonyl or sulphonyl, and
Y represents carbonyl, sulphonyl, —CO—CH$_2$— or —CO—N($R^4$)—,
$R^4$ representing hydrogen, optionally substituted alkyl or aryl, and their physiologically tolerated salts with inorganic or organic acids have good pharmacological properties.

Thus, a resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The new compounds according to the invention, of the formula (I), have particularly excellent effects on the central nervous system, and they have, in particular, anxiolytic, neuroleptic, antidepressant and nootropic efficacy.

The substituted 2-pyrimidinyl-1-piperazine derivative according to the invention are generally defined by formula (I). Preferred compounds are those of the formula (I) in which
A denotes an alkylene group which has 1 to 6 carbon atoms in the chain and is optionally substituted by an alkyl group having 1 to 3 carbon atoms or by a hydroxyl group.,
$R^1$ represents hydrogen, straight-chain or branched alkyl having 1 to 8 (especially 1 to 4) carbon atoms, cyclic alkyl having 3 to 8 (preferably 5 to 6) carbon atoms and optionally substituted by alkoxy or halogen, alkoxy having 1 to 4 carbon atoms, phenoxy, hydroxyl halogen (particularly chlorine, bromine or fluorine) cyano, trifluoromethyl, nitro, amino which is optionally substituted by 1 or 2 alkyl groups each having 1 to 8 (especially 1 to 4) carbon atoms; alkylmercapto having 1 to 4 carbon atoms, phenylmercapto, acylamino (particularly alkanoylamino or alkylsulphonyl amino) having up to 8 carbon atoms, phenyl or 3-indolyl, the phenyl radical for its part being optionally polysubstituted (particularly di- or trisubstituted) by halogen, nitro, amino, hydroxyl, cyano, trifluromethyl, alkyl having 1 to 4 carbon atoms, alkoxy having up to 4 carbon atoms or acylamino (particularly alkanoylamino or alkylsulfonylamino) having up to 8 carbon atoms.
$R^2$ and $R^3$, which can be identical or different, represent hydrogen, straight-chain or branched alkyl having 1 to 9 (especially 1 to 4) carbon atoms, cyclic alkyl having 3 to 8 (preferably 5 to 6) carbon atoms and optionally substituted by halogen, alkoxy having 1 to 4 carbon atoms which is optionally substituted by halogen, mono- or bicyclic carbocyclic aryl, preferably phenyl, which is optionally monosubstituted, disubstituted or polysubstituted by straight-chain or branched alkyl having 1 to 4 carbon atoms, alkoxy having 1 to 4 carbon atoms or nitro, carbamoyl the amide group being substituted optionally by alkyl having 1 to 10 carbon atoms or mono-or bicyclic carbocyclic aryl, preferably phenyl, sulphamoyl, the amide group being substituted optionally by alkyl having 1 to 10 (especially 1 to 4) carbon atoms or mono-or bi-cyclic carbocyclic aryl, preferably phenyl, halogen, hydroxyl, nitro, cyano, alkylmercapto having 1 to 4 carbon atoms, amino which is optionally substituted by alkyl having 1 to 8 (especially 1 to 4) carbon atoms, alkylsulphonamido, the alkyl radical containing 1 to 8 (especially 1 to 4) carbon atoms, arylsulphonamido, in particular one in which aryl represents phenyl, the phenyl radical optionally being substituted by alkyl having 1 to 4 carbon atoms, halogen (especially chlorine, bromine or fluorine), alkoxy, alkylmercapto, hydroxyl, amino, nitro or trifluoromethyl, carboxyl, alkoxycarbonyl, in particular one in which the alkoxy group contains a straight-chain, branched or cyclic alkyl having 1 to 10 carbon atoms, alkoxycarbonylamino, in particular one in which the alkoxy group contains a straight-chain, branched or cyclic alkyl having 1 to 10 carbon atoms, aryloxycarbonylamino, in particular phenoxycarbonylamino, or acylamino particularly $C_1-C_4$-alkanoylamino or $C_1-C_4$-alk having 1 to 10 carbon atoms, X denotes carbonyl or sulphonyl, and Y represents carbonyl, sulphonyl, $-CO-CH_2-$ or $-CO-N(R^4)-$, $R^4$ represents hydrogen, lower alkyl having up to 4 carbon atoms or phenyl, the alkyl and phenyl radicals mentioned in turn being optionally substituted by halogen, trifluoromethyl, nitro, alkyl or alkoxy, each having 1 to 4 carbon atoms. Surprisingly, the new compounds of the formula (I) have pronounced and advantageous effects on the central nervous system. Particular mention may be made of their use as anxiolytic, tranquillising, neuroleptic, antidepressant, antiamnesic and nootropic active compounds and as active compounds improving learning, performance and memory. Furthermore, the new compounds have analgesic and antiinflammatory effects, which can be demonstrated on, for example, the carrageenin-induced oedema of the paws of rats.

The present invention also relates to processes for the preparation of compounds of the formula (I), which comprise (a) alkylating, in the presence of inert solvents at temperatures between 20° and 200° C., where appropriate in the presence of a proton acceptor, pyrimidinylpiperazine derivatives of the formula (II)

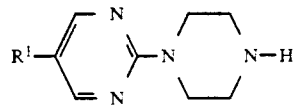
(II)

in which $R^1$ has the abovementioned meaning, with compounds of the formula (III)

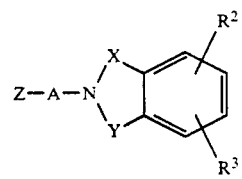
(III)

in which $R^2$, $R^3$, X, Y and A have the abovementioned meaning, and

Z is a suitable leaving group, such as, for example, hydroxyl, chlorine, bromine, iodine, $-OSO_2CH_3$, or

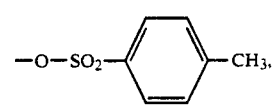

or

A-Z represents

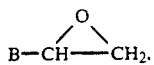

B corresponding to the bridging member A which has been shortened by two terminal carbon atoms, and then, where appropriate, converting the compounds of the formula (I) thus obtained into the acid addition salts in a known manner, or (b) reacting, at elevated temperature between 100° and 250° C. in an inert organic solvent, or without solvent in the melt within the above-mentioned temperature range, aminoalkylpyrimidinylpiperazine derivatives of the formula (IV)

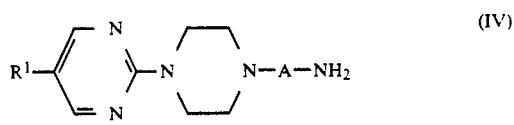
(IV)

in which $R^1$ and A have the abovementioned meaning, with the anhydrides of the formula (V)

(V)

in which $R^2$ and $R^3$ have the abovementioned meaning, and

X and Y, which can be identical or different, denote carbonyl or sulphonyl, or X denotes carbonyl when at the same time Y denotes $-CO-CH_2-$, or (c) reacting, in the presence of inert solvents at temperatures between 20° and 180° C., pyrimidinylpiperazine derivatives of the formula (VI)

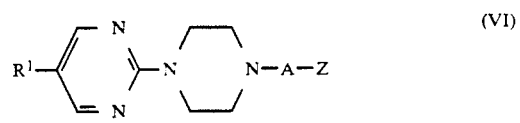
(VI)

in which $R^1$, A and Z have the abovementioned meaning, with compounds of the formula (VII)

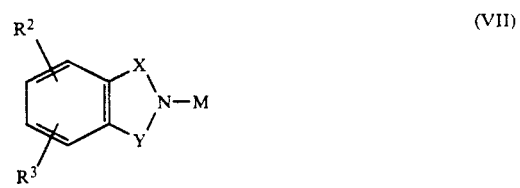
(VII)

in which $R^2$, $R^3$, X and Y have the abovementioned meaning, and

M represents hydrogen or a metal (especially an alkali or alkaline earth metal), preferably sodium, potassium or lithium, or (d) reacting, in the presence of suitable bases in an inert solvent at temperatures between 20° and 180° C., pyrimidinylpiperazine derivatives of the formula (VI-a)

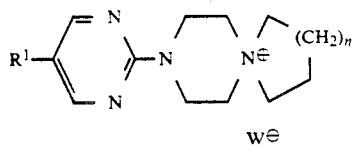

in which
R¹ has the abovementioned meaning, and
W represents chlorine, bromine or iodine, and
n denotes 1 or 2,
with compounds of the formula (VII-a)

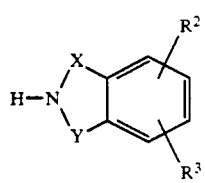

in which
R², R³, X and Y have the abovementioned meaning.

The present invention also relates to a process for the preparation of compounds of the formula

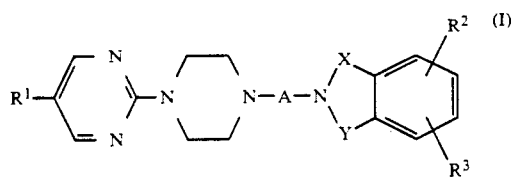

in which
A, R¹, R², R³ and X have the abovementioned meaning, and
Y represents —CO—N(R⁴)—,
which comprises reacting, in the presence of inert solvents at temperatures between 20° and 180° C., or without solvents at temperatures between 50° and 200° C., pyrimidinylpiperazine derivatives of the formula (VIII)

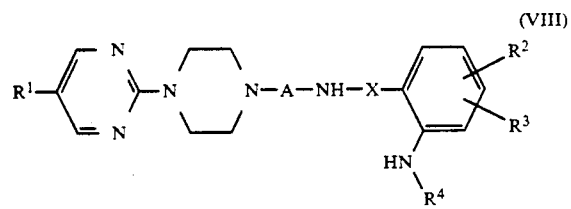

in which
A, R¹, R², R³, R⁴ and X have the above-mentioned meaning,
with the carbonyl compounds of the formula (IX)

in which
R⁵ denotes halogen, alkoxy, amino or imidazolyl, and
R⁶ denotes halogen, trihalogenoalkyl, alkoxy, aryloxy, alkoxycarbonyloxy, amino or imidazolyl.

Particularly important compounds are those of the formula (I)
in which
A represents an alkylene group having 1 to 6 carbon atoms, preferably methylene, ethylene, n-propylene, n-butylene, 2-methyl-n-propylene or 2-hydroxy-n-propylene, where A does not represent the 2-hydroxy-n-propylene group when X and Y represent carbonyl, and R¹, R² and R³ represent hydrogen,
R¹ denotes hydrogen, straight-chain or branched alkyl, preferably methyl, ethyl, propyl, isopropyl, butyl or trifluoromethyl; alkoxy having 1 to 4 carbon atoms, preferably methoxy, ethoxy or trifluoromethoxy; hydroxyl, halogen, preferably fluorine or iodine, cyano, nitro, amino which is optionally substituted by 1 or 2 alkyl groups having 1 to 4 carbon atoms, preferably methyl or ethyl; alkylmercapto having 1 to 4 carbon atoms, preferably methyl; acylamino having 1 to 8 carbon atoms, preferably acetylamino or benzoylamino; 3-indolyl; phenyl, it being possible for the phenyl radical to be monosubstituted or polysubstituted by alkoxy, preferably methoxy or ethoxy; nitro, halogen, preferably chlorine or fluorine, trifluoromethyl; amino, cyano, hydroxyl; alkyl having 1 to 4 carbon atoms, preferably methyl or ethyl; acylamino having up to 8 carbon atoms, preferably acetylamino or benzoylamino,
R² and R³, which can be identical or different, represent hydrogen, straight-chain, branched or cyclic alkyl, preferably methyl, trifluoromethyl, ethyl, propyl, isopropyl, butyl or cyclohexyl; alkoxy having 1 to 4 carbon atoms, preferably methoxy and trifluoromethoxy; aryl, preferably phenyl; hydroxyl, halogen, preferably chlorine or fluorine, cyano, nitro, amino, the nitrogen atom of the amino radical being substituted by 1 or 2 alkyl groups, in particular methyl or ethyl, or being a ring member of a morpholino, piperidino or piperazino radical, alkylsulphonamido, preferably methylsulphonamido; arylsulphonamido, preferably benzenesulphonamido and toluenesulphonamido; carboxyl, alkoxycarbonyl having 1 to 4 carbon atoms in the alkoxy radical, preferably methoxycarbonyl or ethoxycarbonyl; aryloxycarbonylamino, preferably phenoxycarbonylamino; alkylmercapto having 1 to 4 carbon atoms in the alkyl radical, preferably methylmercapto; SCF₃, carbamoyl or sulphamoyl,
X and Y, which can be identical or different, denote carbonyl or sulphonyl, and X alone represents carbonyl or sulphonyl when at the same time Y denotes —CO—CH₂— —CO—N(R⁴)—,
R⁴ representing hydrogen, lower alkyl having up to 4 carbon atoms, preferably methyl, or phenyl.

According to the invention, the new compounds of the formula (I) are obtained by the following processes:
a) reaction of a compound of the general formula (II) with a compound of the general formula (III) in accordance with the scheme below:

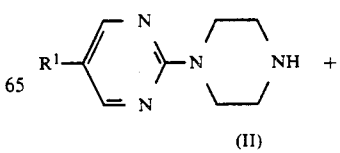

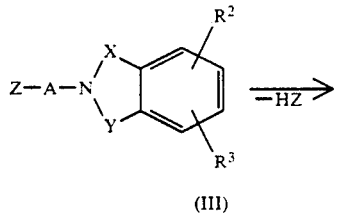

(III)

in which

A, X, Y, Z, $R^1$, $R^2$ and $R^3$ each have the above-mentioned meaning.

The reaction is carried out in solvents which are inert toward each participant in the reaction. These preferably include ethers, such as diethyl ether, diisopropyl ether, tetrahydrofuran, dioxane, ethylene glycol dimethyl ether and ethylene glycol diethyl ether; hydrocarbons, such as ligroin, benzene, toluene, xylene and tetralin, halogenated hydrocarbons, such as chloroform, methylene chloride, chlorobenzene and dichlorobenzenes; nitriles, such as acetonitrile and propionitrile; ketones, such as acetone, diethyl ketone and methyl butyl ketones; carboxamides, such as dimethylformamide, dimethylacetamide, tetramethylurea, hexamethylphosphoric triamide and N-methylpyrrolidone, dimethyl sulphoxide; heterocyclic bases, such as pyridine, quinoline or picolines, as well as commercially available technical mixtures of these solvents.

It is possible to carry out the reaction in an excess of the compounds of the general formulae (II) and or (III) employed, and optionally in the presence of an acid-binding agent, for example an alcoholate, such as potassium tert.-butylate or sodium methylate, an alkali metal hydroxide, such as sodium or potassium hydroxide, an alkaline earth metal hydroxide, such as calcium or barium hydroxide, an alkali metal or alkaline earth metal carbonate, such as sodium carbonate, potassium carbonate, calcium carbonate or sodium or potassium bicarbonate, an alkali metal amide, such as sodium or potassium amide, an alkali metal hydride, such as sodium hydride, tertiary organic bases, such as triethylamine, N,N-dimethylamine, pyridines, quinolines or isoquinolines, or a reaction accelerator, such as potassium iodide, advantageously at temperatures between 0° and 150° C., preferably at temperatures between 0° and 120° C., for example at the boiling point of the solvent used, depending on the reactivity of the radical to undergo nucleophilic exchange. However, it is also possible to carry out the reaction without solvent. However, the reaction is carried out particularly advantageously in the presence of sodium hydride or potassium carbonate.

The reaction is normally carried out under atmospheric pressure.

In carrying out the above process according to the invention, at least 1 mole of the amine of the formula (II) and at least 1 mole of one of the abovementioned acid-binding agents are employed for 1 mole of the compound of the formula (III).

It is also possible and advantageous to carry out the reaction under inert gas, such as nitrogen or argon.

Working up is advantageously carried out by evaporating the reaction solution, taking up the concentrate in a suitable inert organic solvent, where appropriately making alkaline with a base, for example ammonia, sodium carbonate or potassium bicarbonate, and purifying, where appropriate using chromatography on silica gel or aluminium oxide or other suitable adsorbents.

It is possible subsequently to convert compounds of the formula (I), in which the substituent $R^4$ on the nitrogen atom represents hydrogen, into appropriately substituted compounds by known methods. Subsequent substitution of this type is preferably carried out by, for example, converting the NH compound into the alkali metal salt (I, $R^4$=Na, K or Li), using sodium, potassium, sodium amide, potassium amide, potassium hydroxide, lithium hydroxide, sodium hydride or alkali metal alcoholate, such as, for example, sodium methylate or potassium methylate, preferably using sodium hydride, and reacting this salt in a manner known per se with the appropriately substituted halides, such as, for example, alkyl halides, preferably methyl iodide, ethyl iodide, propyl bromide, isopropyl chloride or n-butyl bromide, in particular methyl iodide.

Where the basicity of this group is sufficient, the amide group in compounds of the general formula (I), with $R^4$=H, can optionally also be directly N-alkylated in the presence of suitable proton acceptors, such as trimethylamine, triethylamine, N-methylpiperidine, N,N-dimethylaniline, N,N-diethylaniline, or heterocyclic bases, such as pyridine, picolines, collidines, quinoline or isoquinoline.

The reaction can be carried out without solvent or in the presence of suitable solubilisers. Suitable solubilisers are all organic solvents which are inert toward each reactant. These preferably include aromatic hydrocarbons, such as benzene, toluene, xylene or tetralin, ethers, such as diethyl ether, diisopropyl ether, tetrahydrofuran, dioxane and ethylene glycol diethyl ether, nitriles, such as acetonitrile and propionitrile, carboxamides, such as dimethylformamide and dimethylacetamide, hexamethylphosphoric triamide, N-methylpyrrolidone, dimethyl sulphoxide, heterocyclic bases, such as pyridine, quinoline or picolines, also commercially available technical mixtures of these solvents.

The reaction can be carried out under atmospheric pressure or under elevated pressure, and elevated pressure can be necessary, in particular, for the reaction with low boiling alkyl halides as reactants.

The reaction temperatures can be varied within certain limits. In general, the reaction is carried out at temperatures between 0° and 200° C., preferably between 20° and 150° C., in particular between 40° and 80° C.; room temperature suffices in individual cases.

Working up is then again carried out in analogy to the description above.

Only some of the piperazine derivatives of the formula (II) to be employed as precursors are known, and they can be prepared preferably by methods known per se, for example either in accordance with equation (1):

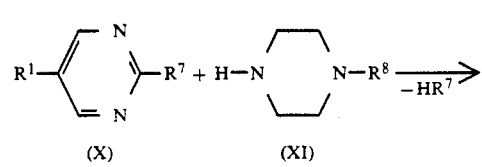

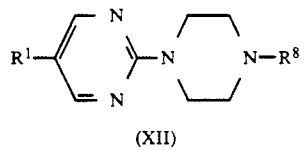

(XII)

by reacting pyrimidine derivatives of the formula (X), in which

R¹ has the meaning indicated in the formula (I), and

R⁷ represents halogen, in particular chlorine, bromine or fluorine, particularly preferably chlorine and fluorine, with known piperazine derivatives of the formula (XI), in which R⁸ represents hydrogen, formyl, alkanoyl, preferably acetyl, propionyl, isopropionyl, butyryl or benzoyl, alkoxycarbonyl, preferably methoxycarbonyl, ethoxycarbonyl, propoxycarbonyl or phenoxycarbonyl, preferably methoxycarbonyl or ethoxycarbonyl, or other suitable protective groups which can readily be eliminated by hydrolysis, in a suitable solvent, such as an alcohol, in particular ethanol, propanol or butanol; a hydrocarbon, such as benzene, toluene or xylene, a carboxamide, such as dimethylformamide or N-methylpyrrolidone, dimethyl sulphoxide, or an ether, such as dioxane ro tetrahydrofuran dimethyl or diethyl ether, by known methods described in the literature (compare K. L. Howard et al., J. Org. Chem. 18, 1484 (1953)) at temperatures between 50° and 150° C., preferably between 70° and 120° C., advantageously in the presence of an acid-binding agent, such as, for example, an alkali metal carbonate, such as triethylamine or pyridine; or in accordance with equation (2):

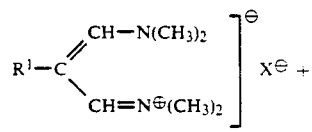

(XIII)

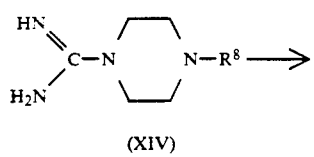

(XIV)

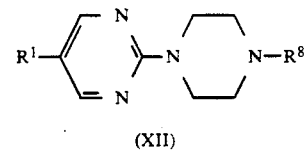

(XII)

by reacting compounds of the formula (XIII), in which

R¹ has the abovementioned meaning, and

X⊖ represents chloride, bromide, sulphate, bisulphate or perchlorate, preferably perchlorate, with the piperazine derivatives of the general formula (XIV), in which R⁸ has the abovementioned meaning, preferably representing methoxycarbonyl or ethoxycarbonyl, by a method known per se (compare R. M. Wagner and C. Jutz, Chem. Ber. 104, 2975 (1971) and G. M. Coppola et al., J. Heterocycl. Chem. 11, 51 (1974)), in a suitable solvent, such as an alcohol, in particular methanol, ethanol, propanol, isopropanol or butanol, or an alcohol-water mixture, at the boiling point of the particular solvent, and working up in a known manner.

The subsequent elimination of the group R⁸ by hydrolysis in accordance with known processes leads to the compounds of the formula (II).

The compounds of the formulae (X) and (XI) are known or are obtained by processes known per se.

The compounds of the formulae (XIII) and (XIV) are likewise known or can be obtained by processes known per se (compare, for example, J. Org. Chem. 13, 144 (1948)).

The invention also relates to the reaction step on which equation (2) is based, in which a compound of the formula (XIII) with a piperazine derivative of the formula (XIV), R⁸ having the abovementioned meaning any particularly preferably representing ethoxycarbonyl, to give compounds of the general formula (XII).

The subsequent elimination, where appropriate, of the protective groups R⁸ used, R⁸ not representing hydrogen, to give the compounds of the formula (II) is preferably carried out by hydrolysis in an aqueous solvent, for example in water, methanol/water, ethanol/water, isopropanol/water or dioxane/water, in the presence of an acid, such as hydrochloric acid or sulphuric acid, or preferably in the presence of an alkali metal base, such as lithium hydroxide, sodium hydroxide or potassium hydroxide, at temperatures between 20° and 100° C., preferably at the boiling point of the reaction mixture. The reaction time is between 1 and 24 hours, preferably between 3 and 12 hours.

The compounds of the formula (III) to be employed as precursors are prepared by methods known per se (compare, for example, H. B. Donahoe et al., J. Org. Chem. 22, 68 (1957)) in accordance with the equation below:

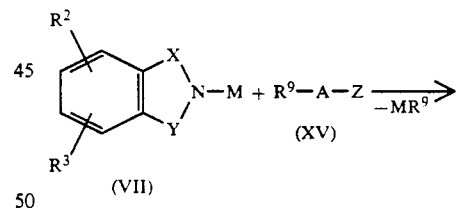

(VII)  (XV)

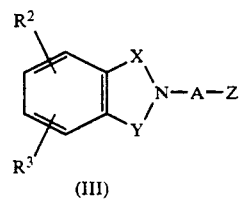

(III)

by reacting suitable compounds of the formula (VII), in which

R², R³, X, Y and M have the abovementioned meaning, with a compound of the formula (XV), in which Z has the abovementioned meaning and preferably represents chlorine and bromine, particularly preferably bromine, A has the abovementioned meaning and particularly preferably represents ethylene, n-propylene, n-butylene, 2-hydroxy-n-propylene or 2-methyl-n-propylene, and R⁹ denotes halogen, preferably chlorine or bromine, particularly preferably bromine, under reaction conditions as are described in the relevant literature.

In the case where

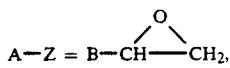

the compound of the formula (VII) is reacted with epichlorohydrin.

The starting materials are reacted in a suitable organic solvent at temperatures between 0° and 150° C., preferably at temperatures between 40° and 120° C., in the presence of an acid-binding agent. Acetonitrile, n-butanol, benzene, toluene, xylene, chlorobenzene, dioxane and tetrahydrofuran, and very particularly dimethylformamide or dimethyl sulphoxide, are preferred examples of organic solvents. The preferred acid-binding agent is potassium carbonate or sodium hydride, but it is also possible to use other inorganic or tertiary organic bases, such as sodium and potassium hydroxide, carbonates, sodium and potassium bicarbonate, or tertiary amines, such as pyridine, quinolines or isoquinolines.

The salts of the formula (VII) which result as intermediates and have, for example, M=sodium, potassium or lithium, can be isolated as the substances; it is more advantageous for the salts to be immediately reacted further in the reaction mixture without previous isolation.

The preparation of the starting materials of the formula (VII) is described in many examples in the literature (compare, for example, H. Hettler, Advances in Heterocyclic Chemistry 15, 234 et seq. (1973)).

The compounds of the formula (XV) which are preferably employed are likewise known from the literature.

b) Reaction of a compound of the formula (IV) with a compound of the formula (V) in accordance with the following equation:

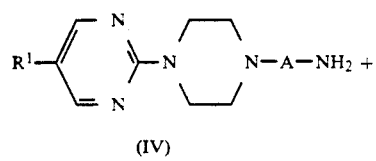

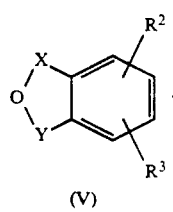

in which

A, X, Y, R¹, R² and R³ have the abovementioned meaning.

The reaction is preferably carried out at elevated temperatures in inert organic solvents, or without solvents in a melt of the reactants, at the same time distilling out the water of reaction. The process is preferably carried out at temperature between 100° and 250° C., in particular in a range between 115° and 170° C. The use of an inert, gas atmosphere is advantageous. Examples of solvents for this reaction which may be mentioned are: tetralin, dichlorobenzene, xylene, N-methylpyrrolidone, pyridine and diethylene glycol dimethyl ether, pyridine being mentioned as particularly preferred. The reaction times are between 1 and 16 hours, preferably between 2 and 6 hours.

In carrying out the process, at least 1 mole of the compound (V) is employed for 1 mole of the compound (IV).

Working up is advantageously carried out in the same manner as described for process variant a).

The ω-aminoalkylpiperazines of the formula (IV) to be employed as precursors can be prepared by methods known per se, for example in accordance with the equation below:

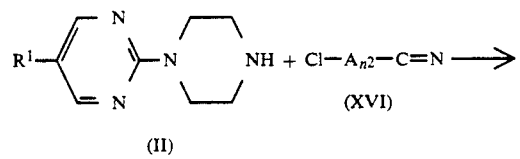

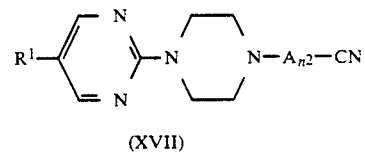

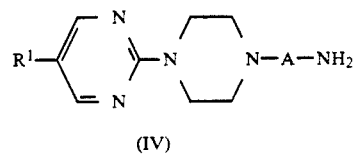

by alkylating compounds of the general formula (II) with known halogenoalkyl nitriles of the general formula (XVI), in which n denotes the number of methylene groups in the alkylene chain, and A has the abovementioned meaning, the group —CH₂—CH(OH)—CH₂— being excluded, and reducing the resulting cyano compounds of the formula (XVII) to give the substituted piperazines (IV). The reduction is preferably carried out in diethyl ether, dioxane or tetrahydrofuran using organometallic compounds, preferably using lithium aluminum hydride. The process is preferably carried out at the boiling points of the abovementioned solvents. The procedures used are described in, for example: X. -H. Wu et al., J. Med. Chem. 12, 876 (1969) and Y. -H. Wu, J. Med. Chem. 15, 477 (1972).

The compounds of the formula (IV) can be prepared by known methods, for example in accordance with the equation below:

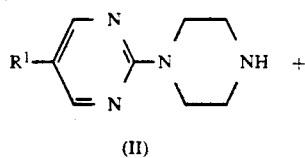

(II)

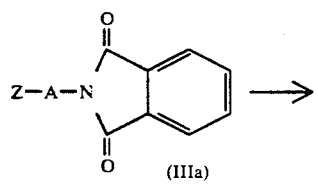

(IIIa)

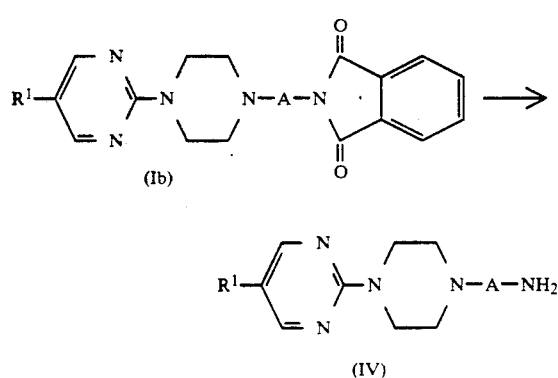

(Ib)

(IV)

Pyridylpiperazines of the formula (II), in which $R^1$ has the abovementioned meaning, are first reacted with compounds of the formula (IIIa), in which A has the abovementioned meaning and particularly preferably represents ethylene, propylene or butylene, and Z has the abovementioned meaning and preferably represents chlorine or bromine, particularly preferably bromine, in the manner described in detail under process a) to give compounds of the formula (Ib). The preparation of compounds of the formula (II) is described in detail above; the compounds of the formula (IIIa) are known and are commercial products; the compounds of the formula (Ib) are new and are, at the same time, special examples of the compounds of the formula (I) according to the invention.

The conversion of compounds of the formula (Ib) into the new ω-ammoalkylpiperazine derivatives of the formula (IV) can be carried out by phthalimide cleavage in a manner known per se, by heating the compounds of the formula (Ib) in mineral acids, preferably in concentrated hydrochloric acid, or by heating with hydrazine hydrate in alcohols containing water, preferably in methanol, ethanol, propanol or isopropanol containing water. The reaction mixtures are worked up in a customary manner (compare J. W. Griffin and D. H. Hey, J. Chem. Soc. 1952, 3334).

The precursors of the formula (V), in which $R^2$, $R^3$, X and Y have the abovementioned meaning, where, preferably, $R^2$ and $R^3$ are identical or different and represent hydrogen or chlorine, X and Y are identical and represent carbonyl, or X represents carbonyl when Y denotes the group $-CO-CH_2-$, can be prepared by known processes.

c) Reaction of a compound of the formula (XVIII) with a compound of the formula (VII) in accordance with the equation below:

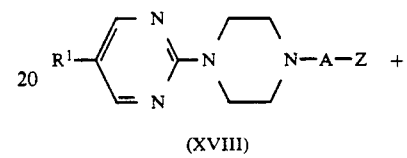

(XVIII)

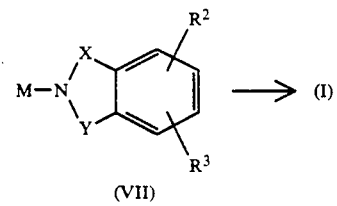

(VII)

in which

A, M, X, Y, Z, $R^1$, $R^2$ and $R^3$ have the abovementioned meaning.

The reaction is carried out, where appropriate, in a solvent of mixture of solvents, for example in acetone, diethyl ketone, acetonitrile, benzene, toluene, xylene, dioxane, tetrahydrofuran, chlorobenzene, tetramethylurea, dimethylformamide, dimethyl sulphoxide, in alcohols, preferably in propanol, butanol, or in mixtures of these alcohols with dimethylformamide, and advantageously, depending on the reactivity of the radical Z, at temperatures between 0° and 150° C., but preferably at the boiling point of the solvent used. The reaction time can be 1 to 48 hours, preferably 2 to 20 hours, depending on the reactivity of the radical Z in (XVIII).

The presence of an acid-binding agent, such as, for example, an alcoholate, such as sodium or potassium methylate or sodium or potassium ethylate an alkali metal hydroxide, such as sodium, potassium or lithium hydroxide, an alkali metal carbonate, such as potassium or sodium carbonate, or potassium or sodium bicarbonate, an alkali metal amide, such as sodium or potassium amide, an alkali metal hydride, such as sodium hydride, or a tertiary organic base, such as triethylamine, pyridine or quinoline, or of a reaction accelerator such as, for example, potassium iodide, is advantageous.

The compounds of the formula (XVIII) employed as precursors can be prepared by methods known per se, for example in accordance with the equation below:

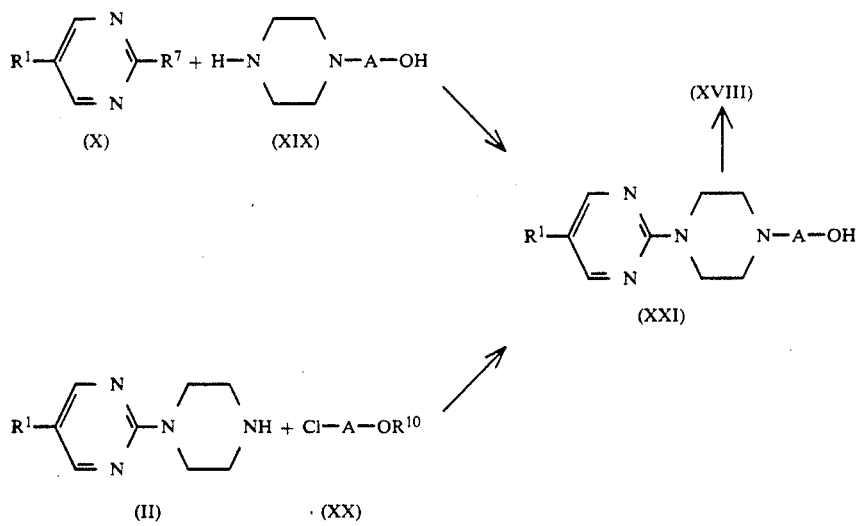

by reacting either compounds of the formula (X), in which

R$^1$ has the abovementioned meaning, and in the present cases preferably represents hydrogen or phenyl, and very particularly preferably represents hydrogen, and R$^7$ denotes halogen, particularly preferably chlorine, with known or commercial hydroxyalkylpiperazines of the formula (XIX), in which A has the abovementioned meaning, and in the present case particularly preferably represents n-propylene, or by reacting compounds of the formula (II), in which R$^1$ has the abovementioned meaning, and in the present case preferably represents hydrogen or phenyl, and very particularly preferably represents hydrogen, with known or commercial compounds of the formula (XX), in which A has the abovementioned meaning, and preferably represents ethylene, propylene or butylene, and very particularly represents butylene, and R$^{10}$ denotes hydrogen or acetyl, and in the present case particularly represents acetyl, under known conditions of alkylation to give compounds of the formula (XXI), preferably without solvent or in inert solvents, such as, for example, acetone, acetonitrile, benzene, toluene, xylene, dioxane, tetrahydrofuran, chlorobenzene, dimethylformamide or dimethyl sulphoxide, at temperatures between 0° and 150° C., preferably at temperatures between 40° and 120° C.

The presence of an acid-binding agent, such as, for example, potassium carbonate or a tertiary organic base, such as, for example, triethylamine or pyridine is advantageous. The mixtures are worked up in a known manner.

The intermediate of the general formula (XXI) is activated by straight forward conventional procedures to form the intermediate (XVIII). For example, the intermediates of the formula (XVIII), in which Z denotes chlorine, are formed by the action of thionyl chloride on the compounds of the formula (XXI).

Bromides and iodides are obtained in a similar manner; tosylates and mesylates corresponding to the formula (XVIII) are obtained by conventional laboratory methods.

d) Reaction of a compound of the formula (VI-a) with a compound of the formula (VII-a) in accordance with the equation below:

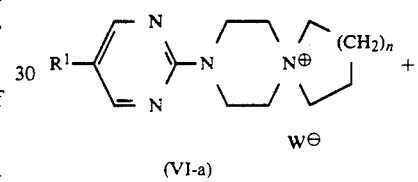

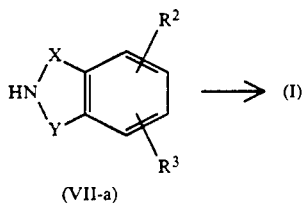

in which

A, W, X, Y, R$^1$, R$^2$ and R$^3$ have the abovementioned meaning.

The reaction is carried out, where appropriate, in a solvent, for example benzene, toluene, xylene, chlorobenzene, acetonitrile, tetramethylurea, dimethylformamide, dimethyl sulphoxide, dibutyl ether, in alcohols, preferably in propanol, n-butanol or amyl alcohol, particularly preferably in n-butanol or dimethylformamide, at temperatures between 20° and 180° C., preferably between 80° and 160° C., particularly preferably at the boiling point of the solvent used. The presence of an acid-binding agent, such as, for example, an alcoholate, such as sodium methylate or sodium ethylate, an alkali metal hydroxide, such as sodium hydroxide or potassium hydroxide, an alkali metal carbonate, such as potassium carbonate, an alkali metal amide, such as sodium amide or potassium amide, an alkali metal hydride, such as sodium hydride, or a tertiary organic base, such as triethylamine or pyridine, is advantageous.

Preferably, molar amounts of the compounds of the formula (VI-a), in which

R$^1$ denotes hydrogen, and

W denotes chlorine or bromine, and n can represent 1 or 2, are reacted with compounds of the formula (VII-a), in which
$R^2$ and $R^3$ have the abovementioned meaning, and
X and Y represent carbonyl or sulphonyl,
in dimethylformamide or n-butanol at the boiling point of the said solvent, in the presence of molar amounts of potassium carbonate. The reaction time can be 2 to 24 hours, preferably 4 to 12 hours. The reaction forms part of the state of the art and is described in British Patent Application GB 2,085,436 A. The compounds of the general formula (VI-a) which are mentioned above as being preferred are known; their preparation is described in the abovementioned application.

The present invention also relates to a process for the preparation of compounds of the formula (Ia), in which
A, X, $R^1$, $R^2$ and $R^3$ have the abovementioned meaning, and
Y represents —CO—N($R^4$)—, $R^4$ preferably representing hydrogen or methyl, by
e) Reaction of a compound of the formula (VIII), in which
$R^1$, $R^2$, $R^3$, $R^4$, A and X have the abovementioned meaning, where, in particular, $R^1$ and $R^2$ preferably represent hydrogen, $R^4$ preferably represents hydrogen or methyl, and A particularly denotes ethylene, propylene or butylene,
with a compound of the formula (IX), in which
$R^5$ and $R^6$ have the abovementioned meaning, where, in particular, $R^5$ and $R^6$ can be identical and represent chlorine or a 2-imidazolyl group, or $R^5$ denotes chlorine and $R^6$ represents ethoxy or phenoxy,
in accordance with the equation below:

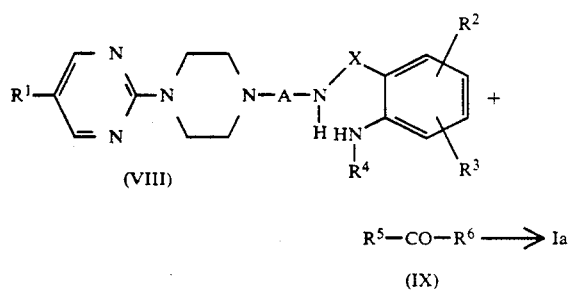

The reaction is advantageously carried out in a solvent, such as, for example, methylene chloride, benzene, toluene, xylene, chlorobenzene, dioxane, tetrahydrofuran or acetonitrile, preferably in toluene or chlorobenzene, advantageously at temperatures between 0° and 150° C., preferably at the boiling point between 40° and 130° C. The reaction can advantageously be carried out in the presence of suitable proton acceptors, such as trimethylamine, triethylamine, N,N-dimethylaniline, heterocyclic bases, such as pyridine, picolines, collidines, quinolines or isoquinoline; triethylamine is preferably used.

In carrying out the process according to the invention, it is advantageous to employ the compound (IX) in an excess of 0.1 to 2 mole per 1 mole of the compound (VIII).

Working up is advantageously carried out by evaporating the reaction solution, taking up the concentrate in a suitable solvent, for example methylene chloride, making alkaline with a suitable base, for example ammonia solution, and purifying, where appropriate using chromatography on silica gel or aluminium oxide or other suitable adsorbents.

The compounds of the formula (VIII) to be employed as precursors

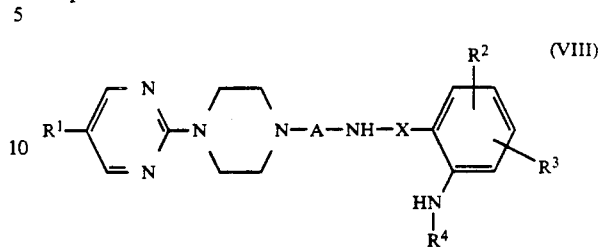

in which
$R^2$, $R^3$ and X have the abovementioned meaning, and represent
$R^1$, $R^4$ and A, the radicals which were mentioned above as being preferred,
are new and the invention likewise relates to them. They may be prepared by reducing the new nitro compounds of the formula (XXII), which are likewise included amongst those to which the invention relates,

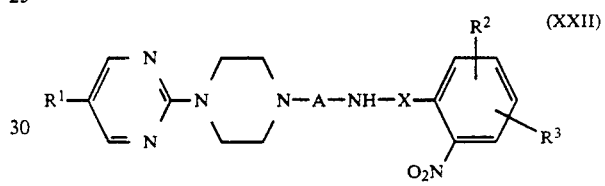

in which
$R^2$, $R^3$ and X have the abovementioned meaning,
$R^1$ preferably represents hydrogen, and
A preferably represents ethylene, propylene or butylene,
with suitable reducing agents to give the amino compounds of the general formula (VIII) (with $R^4$=H).

To prepare (VIII), the nitro compound of the formula (XXII) is dissolved in a suitable solvent, for example in alcohols (especially $C_1$-$C_3$-alkanols), preferably in methanol or ethanol, excess hydrazine hydrate is added in the molar ratio 1:5, preferably in the molar ratio 1:3, and a hydrogenation catalyst, for example palladium, palladium/charcoal or Raney nickel, preferably palladium/charcoal, is added and the mixture is heated at 30° to 100° C. for 0.5 to 5 hours, preferably at 65° to 80° C. for 0.5 to 2 hours.

The reaction mixtures are always worked up in a generally known manner.

The abovementioned new nitro compounds of the formula (XXII) may be prepared in a generally customary and known manner by acylating the new amines of the formula (IV), which are included among those to which the invention relates,

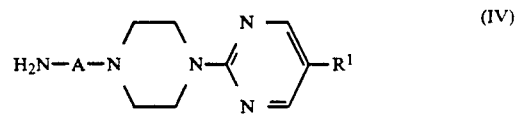

in which
$R^1$ preferably denotes hydrogen, and
A preferably denotes ethylene, propylene or butylene,
with known compounds of the formula (XXIII)

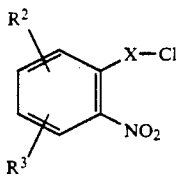
(XXIII)

in which
R², R³ and X have the abovementioned meaning.

The reaction is carried out in a suitable solvent, preferably in toluene, in the presence of an acid-binding agent, for example with triethylamine, pyridine or 10 to 20% strength sodium hydroxide or potassium hydroxide solution. The working up is carried out in a customary manner.

The abovementioned new compounds of the formula (VIII), which are included amongst those to which the invention relates,

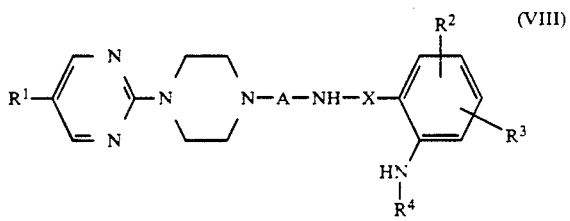
(VIII)

in which
R² and R³ have the abovementioned meaning,
R¹ preferably represents hydrogen, and
R⁴ preferably represents hydrogen or methyl,
may be prepared in the case where
X denotes carbonyl
preferably from the readily accessible isatoic anhydrides of the formula (XXIV)

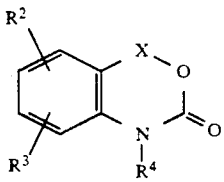
(XXIV)

in which
R² and R³ have the abovementioned meaning,
R⁴ preferably represents hydrogen or methyl, and
X represents carbonyl,
by reaction with the amines of the formula (IV)

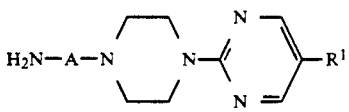
(IV)

in which
R¹ preferably denotes hydrogen, and
A preferably denotes ethylene, propylene or butylene.
The reaction is described by T. Kappe and W. Stadlbauer in: Advances in Heterocyclic Chemistry (Ed.: A. R. Katritzky), Vol. 28, pages 127–182, Academic Press New York, 1981.

Of the intermediates described above, the present invention likewise relates to the pyrimidinylpiperazine derivatives of the formulae (II), (IV) and (XII):

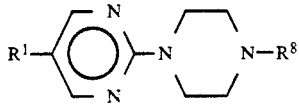
(XII)

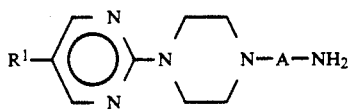
(IV)

Formula (II) corresponds to formula (XII) when $R^8$ denotes hydrogen. In the formulae (II), (IV) and (XII), the radicals have the following meaning:

$R^1$ denotes straight-chain or branched alkyl, preferably methyl, ethyl, propyl, isopropyl, butyl or trifluoromethyl; alkoxy having 1 to 4 carbon atoms, preferably methoxy, ethoxy or trifluoromethoxy; hydroxyl, halogen, preferably fluorine or iodine, cyano, nitro, amino, optionally substituted by 1 or 2 alkyl groups having 1 to 4 carbon atoms, preferably methyl or ethyl; alkylmercapto having 1 to 4 carbon atoms, preferably methyl; acylamino having 1 to 8 carbon atoms, preferably acetylamino or benzoylamino; 3-indolyl; phenyl, it being possible for the phenyl radical to be monosubstituted or polysubstituted by alkoxy, preferably methoxy or ethoxy; nitro, halogen, preferably chlorine or fluorine, trifluoromethyl; amino, cyano, hydroxyl; alkyl having 1 to 4 carbon atoms, preferably methyl or ethyl; acylamino (particularly carboxylic acid acyl) having up to 8 carbon atoms, preferably acetylamino or benzoylamino, where, in the case where $R^8$ denotes hydrogen, $R^1$ does not represent hydroxyl, chlorine, methoxy, phenyl or 3,4-dimethoxyphenyl, $R^8$ denotes hydrogen, alkoxycarbonyl, preferably methoxycarbonyl, ethoxycarbonyl, propoxycarbonyl, isopropoxycarbonyl, butoxycarbonyl or phenoxycarbonyl, where, in the case where $R^1$ represents hydroxyl, chlorine, methoxy, phenyl or 3,4-dimethoxyphenyl, $R^8$ does not denote hydrogen, and A represents an alkylene group having 1 to 6 carbon atoms, preferably methylene, ethylene, n-propylene, n-butylene, 2-methyl-n-propylene or 2-hydroxy-n-propylene.

The abovementioned compounds of the formulae (II), (IV) and (XII) have outstanding effects on the central nervous system, in particular antidepressant and anxiolytic effects; this the invention likewise relates to this use of the abovementioned compounds and their use in appropriate medicaments.

Compounds of the formulae (II), (IV) and (XII), in which
$R^1$ denotes trifluoromethyl, chlorine, fluorine, iodine, 4-methoxyphenyl, 3,4-dimethoxyphenyl, phenyl, 4-chlorophenyl, 3-(trifluoromethyl)phenyl, 2-chloro-6-fluorophenyl or 3-indolyl, $R^1$ not representing chlorine, phenyl or 3,4-dimethoxyphenyl when $R^8$ denotes hydrogen,
$R^8$ preferably represents methoxycarbonyl or ethoxycarbonyl, and particularly preferably represents ethoxycarbonyl, and preferably represents hydrogen when $R^1$ does not denote hydroxyl, chlorine, methoxy, phenyl or 3,4-dimethoxyphenyl, and A represents propylene or n-butylene,
are of very particular importance.

Those new compounds of the formula (II) according to the invention which may be mentioned as being preferred are: 1-(5-fluoro-2-pyrimidinyl)piperazine, 1-(5-iodo-2-pyrimidinyl)piperazine, 1-(5-trifluoromethyl-2-pyrimidinyl)piperazine, 1-(5-(3-indolyl)-2-pyrimidinyl)-piperazine, 1-(5-(4-chlorophenyl)-2-pyrimidinyl)piperazine, 1-(5-(4-methoxyphenyl)-2-pyrimidinyl)piperazine, 1-(5-(3-trifluoromethylphenyl)-2-pyrimidinyl)piperazine and 1-(5-(2-fluoro-6-chlorophenyl)-2-pyrimidinyl)-piperazine.

Those new compounds of the formula (IV) according to the invention which may be mentioned as being preferred are: 1-(4-aminobutyl)-4-(5-phenyl-2-pyrimidinyl)piperazine, 1-(3-aminopropyl)-4-(5-phenyl-2-pyrimidinyl)piperazine, 1-(4-aminobutyl)-4-(5-(4-chlorophenyl)-2-pyrimidinyl)piperazine, 1-(3-aminopropyl)-4-(5-(4-chlorophenyl)-2-pyrimidinyl)piperazine, 1-(4-aminobutyl)-4-(5-(4-methoxyphenyl)-2-pyrimidinyl)piperazine, 1-(3-aminopropyl)-4-(5-(4-methoxyphenyl)-2-pyrimidinyl)piperazine, 1-(4-aminobutyl)-4-(5-(3,4-dimethoxyphenyl)-2-pyrimidinyl)piperazine, 1-(3-aminopropyl)-4-(5-(3,4-dimethoxyphenyl)-2-pyrimidinyl)piperazine, 1-(4-aminobutyl)-4-(5-(3-trifluoromethylphenyl)-2-pyrimidinyl)piperazine, 1-(3-aminopropyl)-4-(5-(3-trifluoromethylphenyl)-2-pyrimidinyl)piperazine, 1-(4-aminobutyl)-4-(5-(2-fluoro-6-chlorophenyl)-2-pyrimidinyl)piperazine, 1-(3-aminopropyl)-4-(5-(2-fluoro-6-chlorophenyl)-2-pyrimidinyl)piperazine, 1-(4-aminobutyl)-4-(5-(3-indolyl)-2-pyrimidinyl)piperazine and 1-(3-aminopropyl)-4-(5-(3-indolyl)-2-pyrimidinyl)-piperazine.

Those new compounds of the formula (XII) according to the invention which may be mentioned as being preferred are: ethyl 4-(5-fluoro-2-pyrimidinyl)-1-piperazinecarboxylate, ethyl 4-(5-chloro-2-pyrimidinyl)-1-piperazinecarboxylate, ethyl 4-(5-iodo-2-pyrimidinyl)-1-piperazinecarboxylate, ethyl 4-(5-trifluoromethyl-2-pyrimidinyl)-1-piperazinecarboxylate, ethyl 4-(5-phenyl-2-pyrimidinyl)-1-piperazinecarboxylate, ethyl 4-(5-(4-chlorophenyl)-2-pyrimidinyl)-1-piperazinecarboxylate, ethyl 4-(5-(4-methoxyphenyl)-2-pyrimidinyl)-1-piperazinecarboxylate, ethyl 4-(5-(3,4-dimethoxyphenyl)-2-pyrimidinyl)-1-piperazinecarboxylate, ethyl 4-(5-(2-chloro-6-fluorophenyl)-2-pyrimidinyl)-1-piperazinecarboxylate, ethyl 4-(5-(3-trifluoromethylphenyl)-2-pyrimidinyl)-1-piperazinecarboxylate and ethyl 4-(5-(3-indolyl)-2-pyrimidinyl-1-piperazinecarboxylate.

The present invention likewise relates to the intermediates of the formula (VIII) described:

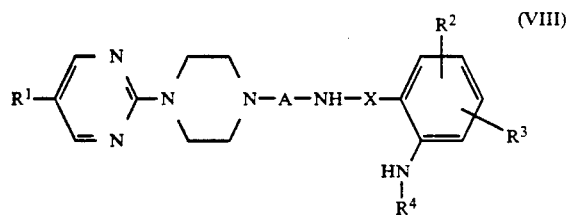

in which
R$^1$ denotes hydrogen, optionally substituted alkyl, aralkyl, halogen, hydroxyl, nitro, cyano, optionally substituted alkoxy, optionally substituted aryl or heteroaryl, alkylamino or arylamino, alkylmercapto or acylamino, R$^2$ and R$^3$, which can be identical or different, represent hydrogen, optionally substituted alkyl, optionally substituted aryl, aralkyl, cycloalkyl, optionally substituted alkoxy, phenoxy, halogen, hydroxyl, alkylamino, arylamino, nitro, alkylmercapto, cyano, carboxyl, alkoxycarbonyl, optionally substituted carbamoyl or optionally substituted sulphamoyl, R$^4$ represents hydrogen, optionally substituted (such as C$_1$-C$_6$ and especially C$_1$-C$_4$-alkyl or aryl, especially mono- or bi-cyclic carbocyclic aryl A represents an optionally substituted alkylidene radical, X denotes carbonyl or sulphonyl, and NHR$^4$ can also denote NO$_2$, the definitions for R$^1$, R$^2$ and R$^3$ can be defined in the manners provided above with respect to the analogous substituents provided for those terms in compound (I).

The above mentioned compounds of the formula (VIII) have useful effects on the central nervous system, in particular antidepressant and anxiolytic effects; thus the invention likewise relates to their use in this respect and their use in appropriate medicaments.

Compounds of the formula (VIII), in which
R$^1$ denotes hydrogen, chlorine, fluorine, iodine or phenyl,
R$^2$ and R$^3$, which can be identical or different, represent hydrogen and chlorine,
R$^4$ denotes hydrogen or methyl,
A represents n-propylene or n-butylene,
X denotes carbonyl or sulphonyl, and
NHR$^4$ can also denote NO$_2$,
are of very particular importance.

Those new compounds of the general formula (VIII) according to the invention which may be mentioned as being preferred are: N-(3-(4-(2-pyrimidinyl)-1-piperazinyl)propyl)-2-aminobenzamide, N-(4-(4-(2-pyrimidinyl)-1-piperazinyl)butyl-2-aminobenzamide, N-(3-(4-(2-pyrimidinyl)-1-piperazinyl)propyl)-2-amino-5-chlorobenzamide, N-(4-(4-(2-pyrimidinyl)-1-piperazinyl)butyl)-2-amino-5-chlorobenzamide, N-(3-(4-(2-pyrimidinyl)-1-piperazinyl)propyl)-2-methylaminobenzamide, N-(4-(4-(2-pyrimidinyl)-1-piperazinyl)butyl)-2-methylaminobenzamide, N-(4-(4-(2-pyrimidinyl)-1-piperazinyl)butyl)-2-nitrobenzenesulphonamide, N-(3-(4-(2-pyrimidinyl)-1-piperazinyl)propyl-2-nitrobenzenesulphonamide, N-(4-(4-(2-pyrimidinyl)-1-piperazinyl)butyl-2-aminobenzenesulphonamide and N-(3-(4-(2-pyrimidinyl)-1-piperazinyl)-propyl-2-aminobenzenesulphonamide.

Compounds of the formula (I), in which
A denotes ethylene, n-propylene, n-butylene or 2-hydroxy-n-propylene, where A does not represent 2-hydroxy-n-propylene when X and Y represent carbonyl and R$^1$, R$^2$ and R$^3$ represent hydrogen,
R$^1$ denotes hydrogen, chlorine, fluorine, iodine, 4-methoxyphenyl, 3,4-dimethoxyphenyl, phenyl, 4-chlorophenyl, 3-(trifluoromethyl)phenyl, 2-chloro-6-fluorophenyl or 3-indolyl,
R$^2$ and R$^3$ are identical or different and represent hydrogen, fluorine, chlorine or nitro,
X represents carbonyl and sulphonyl, and
Y represents carbonyl, sulphonyl, —CO—CH$_2$— or —CO—N(R$^4$)—, where R$^4$ denotes hydrogen, phenyl or methyl,
are of very particular importance.

In combination with the other radicals mentioned, Y very particularly preferably denotes carbonyl, sulphonyl, —CO—CH$_2$ or —CO—N(R$^4$), the —CO— group being adjacent to the nitrogen atom in each instance and R$^4$ denoting hydrogen, phenyl or methyl.

Specific new active compounds according to the invention which may be mentioned are: 2-(4-(4-(2-pyrimidinyl)-1-piperazinyl)butyl)-5-fluoro-1,2-benzisothiazol-3(2H)one 1,1-dioxide, 2-(3-(4-(2-pyrimidinyl)-1-piperazinyl)propyl)-1,2-benzisothiazol-3(2H)one 1,1-dioxide, 2-(4-(4-(5-fluoro-2-pyrimidinyl)-1-piperazinyl)butyl)-1,2-benzisothiazol-3(2H)one 1,1-dioxide, 2-(3-(4-(2-pyrimidinyl)-1-piperazinyl)propyl-5-fluoro-1,2-benzisothiazol-3(2H)one 1,1-dioxide, 2-(4-(4-(5-(3-trifluoromethylphenyl)-2-pyrimidinyl)-1-piperazinyl)butyl)-1,2-benzisothiazol-3(2H)one 1,1-dioxide, 2-(4-(4-(5-hydroxy-2-pyrimidinyl)-1-piperazinyl)butyl)-1,2-benzisothiazol-3(2H)one 1,1-dioxide, 2-(4-(4-(5-chloro-2-pyrimidinyl)-1-piperazinyl)butyl)-1,2-benzisothiazol-3(2H)one 1,1-dioxide, 2-(3-(4-(5-phenyl-2-pyrimidinyl)-1-piperazinyl)propyl)-1,2-benzisothiazol-3(2H)one 1,1-dioxide, 2-(3-(4-(5-fluoro-2-pyrimidinyl)-1-piperazinyl)propyl-1,2-benzisothiazol-3(2H)one 1,1-dioxide, 2-(4-(4-(5-methoxy-2-pyrimidinyl)-1-piperazinyl)butyl)-1,2-benzisothiazol-3(2H)one 1,1-dioxide, 2-(3-(4-(5-methoxy-2-pyrimidinyl)-1-piperazinyl)propyl)-1,2-benzisothiazol-3(2H)one 1,1-dioxide, 2-(3-(4-(2-pyrimidinyl)-1-piperazinyl)-2-hydroxypropyl)-1,2-benzisothiazol-3(2H)one 1,1-dioxide, 2-(3-(4-(5-phenyl-2-pyrimidinyl)-1-piperazinyl)-2-hydroxypropyl)-1,2-benzisothiazol-3(2H)one 1,1-dioxide, 2-(3-(4-(5-fluoro-2-pyrimidinyl)-1-piperazinyl)-2-hydroxypropyl)-1,2-benzisothiazol-3(2H)one 1,1-dioxide, 2-(3-(4-(5-(4-chlorophenyl)-2-pyrimidinyl)-1-piperazinyl)-2-hydroxypropyl)-1,2-benzisothiazol-3(2H)one 1,1-dioxide, 2-(3-(4-(2-pyrimidinyl)-1-piperazinyl)propyl)5-ethyloxycarbonylamino-1,2-benzisothiazol-3(2H)one 1,1-dioxide, 2-(4-(4-(2-pyrimidinyl)-1-piperazinyl)butyl)-1,2-benzisothiazol-3(2H)one 1,1-dioxide, 2-(4-(4-(2-pyrimidinyl)-1-piperazinyl)butyl)-5-ethyloxycarbonylamino-1,2-benzisothiazol-3(2H)one 1,1-dioxide, 2-(3-(4-(2-pyrimidinyl)-1-piperazinyl)propyl)-5-isopropyloxycarbonylamino-1,2-benzisothiazol-3(2H)one 1,1-dioxide, 2-(4-(4-(2-pyrimidinyl)-1-piperazinyl)butyl)-5-isopropyloxycarbonylamino-1,2-benzisothiazol-3(2H)one 1,1-dioxide, 2-(4-(4-(2-pyrimidinyl-1-piperazinyl)butyl)-6-ethoxycarbonylamino-1,2-benzisothiazol-3(2H)one 1,1-dioxide, 2-(3-(4-(2-pyrimidinyl)-1-piperazinyl)propyl)-6-fluoro-1,2-benzisothiazol-3(2H)one 1,1-dioxide, 2-(4-(4-(2-pyrimidinyl)-1-piperazinyl)butyl)-6-fluoro-1,2-benzisothiazol-3(2H)one 1,1-dioxide, 2-(3-(4-(2-pyrimidinyl)-1-piperazinyl)propyl)-5-methylthio-1,2-benzisothiazol-3(2H)one 1,1-dioxide, 2-(4-(4-(2-pyrimidinyl)-1-piperazinyl)butyl)-5-methylthio-1,2-benzisothiazol-3(2H)one 1,1-dioxide, 2-(3-(4-(2-pyrimidinyl)-1-piperazinyl)propyl)-5-trifluoromethoxy-1,2-benzisothiazol-3(2H)one 1,1-dioxide, 2-(4-(4-(2-pyrimidinyl)-1-piperazinyl)butyl)-5-trifluoromethoxy-1,2-benzisothiazol-3(2H)one 1,1-dioxide, 2-(4-(4-(2-pyrimidinyl)-1-piperazinyl)butyl)-5-chloro-6-trifluoromethyl-1,2-benzisothiazol-3(2H)one 1,1-dioxide, 2-(3-(4-(2-pyrimidinyl)-1-piperazinyl)propyl)-5-methylsulphonylamino-1,2-benzisothiazol-3(2H)one 1,1-dioxide, 2-(4-(4-(2-pyrimidinyl)-1-piperazinyl)butyl)-5-methylsulphonylamino-1,2-benzisothiazol-3(2H)one 1,1-dioxide, 2-(4-(4-(2-pyrimidinyl)-1-piperazinyl)butyl)-5-(4-methylphenyl)-sulphonylamino-1,2-benzisothiazol-3(2H)one 1,1-dioxide, 2-(3-(4-(2-pyrimidinyl)-1-piperazinyl)propyl)-5-(4-methylphenyl)sulphonylamino-1,2-benzisothiazol-3(2H)one 1,1-dioxide, 2-(3-(4-(2-pyrimidinyl)-1-piperazinyl)propyl)-6-methylsulphonylamino-1,2-benzisothiazol-3(2H)one 1,1-dioxide, 2-(4-(4-(2-pyrimidinyl)-1-piperazinyl)butyl)-6-methylsulphonylamino-1,2-benzisothiazol-3(2H)one dioxide, 2-(4-(4-(2-pyrimidinyl)-1-piperazinyl)butyl)-6-bis(methanesulphonyl)amino-1,2-benzisothiazol-3(2H)one 1,1-dioxide, 2-(3-(4-(5-(4-chlorophenyl)-2-pyrimidinyl)-1-piperazinyl)propyl)-1,2-benzisothiazol-3(2H)one 1,1-dioxide, 2-(2-(4-(5-(4-chlorophenyl)-2-pyrimidinyl)-1-piperazinyl)ethyl)-1,2-benzisothiazol-3(2H)one 1,1-dioxide, 2-(4-(4-(2-pyrimidinyl)-1-piperazinyl)butyl)-6-(4-methylphenyl)sulphonylamino-1,2-benzisothiazol-3(2H)one 1,1-dioxide, 2-(3-(4-(2-pyrimidinyl)-1-piperazinyl)propyl)-6-(4-methylphenyl)sulphonylamino-1,2-benzisothiazol-3(2H)one 1,1-dioxide, 2-(4-(4-(2-pyrimidinyl)-1-piperazinyl)butyl)-5-sulphamoyl-1,2-benzisothiazol-3(2H)one 1,1-dioxide, 2-(3-(4-(2-pyrimidinyl)-1-piperazinyl)propyl)-5-sulphamoyl-1,2-benzisothiazol-3(2H)one 1,1-dioxide, 2-(4-(4-(2-pyrimidinyl)-1-piperazinyl)butyl)-6-sulphamoyl-1,2-benzisothiazol-3(2H)one 1,1-dioxide, 2-(3-(4-(2-pyrimidinyl)-1-piperazinyl)propyl)-6-sulphamoyl-1,2-benzisothiazol-3(2H)one 1,1-dioxide, 2-(4-(4-(2-pyrimidinyl)-1-piperazinyl)butyl)-6-amino-1,2-benzithiazol-3(2H)one 1,1-dioxide, 2-(4-(4-(2-pyrimidinyl)-1-piperazinyl)butyl)-5-amino-1,2-benzisothiazol-3(2H)one 1,1-dioxide, 2-(4-(4-(2-pyrimidinyl)-1-piperazinyl)butyl)-5-nitro-1,2-benzisothiazol-3(2H)one 1,1-dioxide, 2-(3-(4-(2-pyrimidinyl)-1-piperazinyl)propyl)-6-amino-1,2-benzisothiazol-3(2H)one 1,1-dioxide, 2-(3-(4-(2-pyrimidinyl)-1-piperazinyl)propyl)-6-nitro-1,2-benzisothiazol-3(2H)one 1,1-dioxide, 2-(3-(4-(2-pyrimidinyl)-1-piperazinyl)propyl)-5-nitro-1,2-benzisothiazol-3(2H)one 1,1-dioxide, 2-(3-(4-(2-pyrimidinyl)-1-piperazinyl)propyl)-5-amino-1,2-benzisothiazol-3(2H)one 1,1-dioxide, 2-(3-(4-(2-pyrimidinyl)-1-piperazinyl)propyl)-6-acetylamino-1,2-benzisothiazol-3(2H)one 1,1-dioxide, 2-(4-(4-(2-pyrimidinyl)-1-piperazinyl)butyl)-6-acetylamino-1,2-benzisothiazol-3(2H)one 1,1-dioxide, 2-(3-(4-(2-pyrimidinyl)-1-piperazinyl)propyl)-5-acetylamino-1,2-benzisothiazol-3(2H)one 1,1-dioxide, 2-(4-(4-(2-pyrimidinyl)-1-piperazinyl)butyl)-5-acetylamino-1,1-benzisothiazol-3(2H)one 1,1-dioxide, 2-(2-(4-(2-pyrimidinyl)-1-piperazinyl)ethyl)-1,2-benzisothiazol-3(2H)one 1,1-dioxide, 2-(3-(4-(2-pyrimidinyl)-1-piperazinyl)-2-hydroxypropyl)-6-trifluoromethyl-5-chloro-1,2-benzisothiazol-3(2H)one 1,1-dioxide, 2-(4-(4-(2-pyrimidinyl)-1-piperazinyl)butyl)-5-trifluoromethyl-1,2-benzisothiazol-3(2H)one 1,1-dioxide, 2-(3-(4-(2-pyrimidinyl)-1-piperazinyl)propyl)-5-trifluoromethyl-1,2-benzisothiazol-3(2H)one 1,1-dioxide, 2-(4-(4-(2-pyrimidinyl)-1-piperazinyl)butyl)-5-methyl-1,2-benzisothiazol-3(2H)one 1,1-dioxide, 2-(3-(4-(2-pyrimidinyl)-1-piperazinyl)propyl)-5-methyl-1,2-benzisothiazol-3(2H)one 1,1-dioxide, 2-(3-(4-(2-pyrimidinyl)-1-piperazinyl)propyl-6,7-dimethyl-1,2-benzisothiazol-3(2H)one 1,1-dioxide, 2-(3-(4-(2-pyrimidinyl)-1-piperazinyl)butyl)-6,7-dimethyl-1,2-benzisothiazol-3(2H)one 1,1-dioxide, 2-(3-(4-(2-pyrimidinyl)-1-piperazinyl)-2-hydroxypropyl)-5-methoxy-1,2-benzisothiazol-3(2H)one 1,1-dioxide, 2-(3-(4-(2-pyrimidinyl)-1-piperazinyl)propyl)-6-methoxy-1,2-benzisothiazol-3(2H)one 1,1-dioxide, 2-(4-(4-(2-pyrimidinyl)-1-piperazinyl)butyl)-6-methoxy-1,2-benzisothiazol- 3(2H)one 1,1-dioxide, 2-(4-(4-(2-pyrimidinyl)-1-piperazinyl)butyl)-5-methoxy-1,2-benzisothiazol-3(2H)one 1,1-dioxide, 2-(4-(4-(5-iodo-2-pyrimidinyl)-1-piperazinyl)butyl-1,2-benzisothiazol-3(2H)one 1,1-dioxide, 2-(4-(4-(2-pyrimidinyl)-1-piperazinyl)butyl)-6-nitro-1,2-benzisothiazol-3(2H)one 1,1-dioxide, 2-(4-(4-(2-pyrimidinyl)-1-piperazinyl)butyl)-5-chloro-1,2-benzisothiazol-3(2H)one 1,1-dioxide, 2-(4-(4-(5-phenyl-2-pyrimidinyl)-1-piperazinyl)butyl)-1,2-benzisothiazol-3(2H)one 1,1-dioxide, 2-(4-(4-(5-phenyl-2-pyrimidinyl)-1-piperazinyl)butyl-6-chloro-1,2-benzisothiazol-3(2H)one 1,1-dioxide, 2-(4-(4-(2-pyrimidinyl)-1-piperazinyl)butyl)isoquinoline-1,3(2H,4H)dione, 2-(4-(4-(5-(3,4-dimethoxyphenyl)-2-pyrimidinyl)-1-piperazinyl)butyl)isoquinoline-1,3(2H,4H)dione, 2-(3-(4-(2-pyrimidinyl)-1-piperazinyl)propyl)isoquinoline-1,3(2H,4H)dione, 2-(3-(4-(5-phenyl-2-pyrimidinyl)-1-piperazinyl)propyl)isoquinoline-1,3(2H,4H)dione, 2-(3-(4-(2-pyrimidinyl)-1-piperazinyl)-2-hydroxypropyl)isoquinoline-1,3(2H,4H)dione, 2-(3-(4-(5-phenyl-2-pyrimidinyl)-1-piperazinyl)-2-hydroxypropyl)isoquinoline-1,3(2H,4H)dione, 2-(2-(4-(2-pyrimidinyl)-1-piperazinyl)ethyl)-1,3,2-benzodithiazole 1,1,3,3-tetroxide, 2-(3-(4-(2-pyrimidinyl)-1-piperazinyl)propyl)-1,3,2-benzodithiazole 1,1,3,3-tetroxide, 2-(4-(4-(2-pyrimidinyl)-1-piperazinyl)butyl)-1,3,2-benzodithiazole 1,1,3,3-tetroxide, 2-(3-(4-(2-pyrimidinyl)-1-piperazinyl)-2-hydroxypropyl)-1,3,2-benzodithiazole 1,1,3,3-tetroxide, 2-(4-(4-(5-fluoro-2-pyrimidinyl)-1-piperazinyl)butyl)-1,3,2-benzodithiazole 1,1,3,3-tetroxide, 2-(4-(4-(5-phenyl-2-pyrimidinyl)-1-piperazinyl)butyl)-1,3,2-benzodithiazole 1,1,3,3-tetroxide, 2-(4-(4-(5-(4-chlorophenyl)-2-pyrimidinyl)-1-piperazinyl)butyl)-1,3,2-benzodithiazole 1,1,3,3-tetroxide, 2-(4-(4-(5-(3-trifluoromethylphenyl)-2-pyrimidinyl)-1-piperazinyl)butyl)-1,3,2-benzodithiazole 1,1,3,3-tetroxide, 2-(4-(4-(5-(4-methoxyphenyl)-2-pyrimidinyl)-1-piperazinyl)butyl)-1,3,2-benzodithiazole 1,1,3,3-tetroxide, 3-(3-(4-(2-pyrimidinyl)-1-piperazinyl)propyl)quinazoline-2,4(1H,3H)dione, 3-(4-(4-(2-pyrimidinyl)-1-piperazinyl)butyl)quinazoline-2,4(1H,3H)dione, 3-(3-(4-(2-pyrimidinyl)-1-piperazinyl)propyl)-6-chloroquinazoline-2,4(1H,3H)dione, 3-(4-(4-(2-pyrimidinyl)-1-piperazinyl)butyl)-6-chloroquinazoline-2,4(1H,3H)dione, 3-(3-(4-(2-pyrimidinyl)-1-piperazinyl)propyl)-1-methylquinazoline-2,4(1H,3H)dione, 3-(4-(4-(2-pyrimidinyl)-1-piperazinyl)butyl)-1-methyl-6-chloroquinazoline-2,4(1H,3H)dione, 3-(3-(4-(2-pyrimidinyl)-1-piperazinyl)propyl)-7-fluoroquinazoline-2,4(1H,3H)dione, 3-(4-(4-(2-pyrimidinyl)-1-piperazinyl)butyl)-7-fluoro-1-methylquinazoline-2,4(1H,3H)dione, 3-(3-(4-(2-pyrimidinyl)-1-piperazinyl)propyl)-6-fluoroquinazoline-2,4(1H,3H)dione, 3-(4-(4-(2-pyrimidinyl)-1-piperazinyl)butyl)-6-fluoroquinazoline-2,4(1H,3H)dione, 3-(3-(4-(2-pyrimidinyl)-1-piperazinyl)-2-hydroxypropyl)-1-methylquinazoline-2,4(1H,3H)dione, 2-(3-(4-(2-pyrimidinyl)-1-piperazinyl)-2-hydroxypropyl)-6-fluoro-1-methylquinazoline-2,4(1H,3H)dione, 3-(3-(4-(2-pyrimidinyl)-1-piperazinyl)propyl-6-methylthioquinazoline-2,4(1H,3H)dione, 3-(4-(4-(2-pyrimidinyl)-1-piperazinyl)butyl)-6-methylthioquinazoline-2,4(1H,3H)dione, 3-(4-(4-(5-phenyl-2-pyrimidinyl)-1-piperazinyl)butyl)quinazoline-2,4(1H,3H)dione, 3-(3-(4-(2-pyrimidinyl)-1-piperazinyl)propyl)-6-trifluoromethylquinazoline-2,4(1H,3H)dione, 3-(4-(4-(2-pyrimidinyl)-1-piperazinyl)butyl)-6-trifluoromethylquinazoline-2,4(1H,3H)dione, 3-(4-(4-(2-pyrimidinyl)-1-piperazinyl)propyl)-6-trifluoromethoxyquinazoline-2,4(1H,3H)dione, 3-(4-(4-(2-pyrimidinyl)-1-piperazinyl)butyl)-6-trifluoromethoxyquinazoline-2,4(1H,3H)dione, 3-(3-(4-(2-pyrimidinyl)-1-piperazinyl)propyl)-6-chloro-7-trifluoromethylquinazoline-2,4(1H,3H)dione, 3-(4-(4-(2-pyrimidinyl)-1-piperazinyl)butyl)-6-chloro-7-trifluoromethylquinazoline-2,4(1H,3H)dione, 3-(3-(4-(2-pyrimidinyl)-1-piperazinyl)propyl)-6-nitroquinazoline-2,4(1H,3H)dione, 3-(4-(4-(2-pyrimidinyl)-1-piperazinyl)butyl)-6-nitroquinazoline-2,4(1H,3H)dione, 3-(3-(4-(2-pyrimidinyl)-1-piperazinyl)propyl)-7-nitroquinazoline-2,4(1H,3H)dione, 3-(4-(4-(2-pyrimidinyl)-1-piperazinyl)butyl)-7-nitroquinazoline-2,4(1H,3H)dione, 3-(3-(4-(2-pyrimidinyl)-1-piperazinyl)propyl)-6-aminoquinazoline-2,4(1H,3H)dione, 3-(4-(4-(2-pyrimidinyl)-1-piperazinyl)butyl)-6-aminoquinazoline-2,4(1H,3H)dione, 3-(3-(4-(2-pyrimidinyl)-1-piperazinyl)propyl)-7-aminoquinazoline-2,4(1H,3H)dione, 3-(4-(4-(2-pyrimidinyl)-1-piperazinyl)butyl)-7-aminoquinazoline-2,4(1H,3H)dione, 3-(3-(4-(2-pyrimidinyl)-1-piperazinyl)propyl)-6-acetylaminoquinazoline-2,4(1H,3H)dione, 3-(4-(4-(2-pyrimidinyl)-1-piperazinyl)butyl)-6-acetylaminoquinazoline-2,4(1H,3H)dione, 3-(3-(4-(2-pyrimidinyl)-1-piperazinyl)propyl)-7-acetylaminoquinazoline-2,4(1H,3H)dione, 3-(4-(4-(2-pyrimidinyl)-1-piperazinyl)butyl)-7-acetylaminoquinazoline-2,4(1H,3H)dione, 2-(3-(4-(2-pyrimidinyl)-1-piperazinyl)propyl)-1,2,4-benzothiadiazin-3(4H)one 1,1-dioxide, 2-(3-(4-(2-pyrimidinyl)-1-piperazinyl)propyl)-4-methyl-1,2,4-benzothiadiazin-3(4H)one 1,1-dioxide, 2-(3-(4-(2-pyrimidinyl)-1-piperazinyl)propyl)-4-ethyl-1,2,4-benzothiadiazin-3(4H)one 1,1-dioxide, 2-(4-(4-(2-pyrimidinyl)-1-piperazinyl)butyl)-4-methyl-1,2,4-benzothiadiazin-3(4H)one 1,1-dioxide, 2-(4-(4-(2-pyrimidinyl)-1-piperazinyl)butyl)-4-ethyl-1,2,4-benzothiadiazin-3(4H)one 1,1-dioxide, 2-(2-(4-(2-pyrimidinyl)-1-piperazinyl)ethyl)-1,2,4-benzothiadiazin-3(4H)one 1,1-dioxide, 2-(4-(4-(2-pyrimidinyl)-1-piperazinyl)butyl)-1,2,4-benzothiadiazin-3(4H)one 1,1-dioxide, 2-(3-(4-(2-pyrimidinyl)-1-piperazinyl)propyl)-4-phenyl-1,2,4-benzothiadiazin-3(4H)one 1,1-dioxide, 2-(4-(4-(2-pyrimidinyl)-1-piperazinyl)butyl)-4-phenyl-1,2,4-benzothiadiazin-3(4H)one 1,1-dioxide, 2-(3-(4-(2-pyrimidinyl)-1-piperazinyl)-2-hydroxypropyl)-1,2,4-benzothiadiazin-3(4H)one 1,1-dioxide, 2-(3-(4-(2-pyrimidinyl)-1-piperazinyl)propyl)-7-fluoro-1,2,4-benzothiadiazin-3(4H)one 1,1-dioxide, 2-(3-(4-(2-pyrimidinyl)-1-piperazinyl)propyl)-7-fluoro-4-methyl-1,2,4-benzothiadiazin-3(4H)one 1,1-dioxide, 2-(3-(4-(2-pyrimidinyl)-1-piperazinyl)propyl)-7-cyano-1,2,4-benzothiadiazin-3(4H)one 1,1-dioxide, 2-(4-(4-(2-pyrimidinyl)-1-piperazinyl)butyl)-7-cyano-1,2,4-benzothiadiazin-3(4H)one 1,1-dioxide, 2-(3-(4-(2-pyrimidinyl)-1-piperazinyl)propyl)-7-trifluoromethoxy-1,2,4-benzothiadiazin-3(4H)one 1,1-dioxide, 2-(4-(4-(2-pyrimidinyl)-1-piperazinyl)butyl)-7-trifluoromethoxy-4-methyl-1,2,4-benzothiadiazin-3(4H)one 1,1-dioxide, 2-(3-(4-(2-pyrimidinyl)-1-piperazinyl)propyl)-7-isopropyl-1,2,4-benzothiadiazin-3(4H)one 1,1-dioxide, 2-(3-(4-(2-pyrimidinyl)-1-piperazinyl)propyl-7-isopropyl-4-ethyl-1,2,4-benzothiadiazin-3(4H)one 1,1-dioxide, 2-(3-(4-(2-pyrimidinyl)-1-piperazinyl)propyl-7-cyclohexyl- 1,2,4-benzothiadiazin-3(4H)one 1,1-dioxide, 2-(3-(4-(2-pyrimidinyl)-1-piperazinyl)propyl)-7-chloro-1,2,4-benzothiadiazin-3(4H)one 1,1-dioxide, 2-(4-(4-(2-pyrimidinyl)-1-piperazinyl)butyl)-7-chloro-1,2,4-benzothiadiazin-3(4H)one 1,1-dioxide, 2-(3-(4-(5-phenyl-2-pyrimidinyl)-1-piperazinyl)propyl)-7-chloro-1,2,4-benzothiadiazin-3(4H)one 1,1-dioxide, 2-(3-(4-(2-pyrimidinyl)-1-piperazinyl)-2-hydroxypropyl)-7-chloro-1,2,4-benzothiadiazin-3(4H)one 1,1-dioxide, 2-(3-(4-(2-pyrimidinyl)-1-piperazinyl)propyl)-6-methyl-1,2,4-benzothiadiazin-3(4H)one 1,1-dioxide, 2-(4-(4-(2-pyrimidinyl)-1-piperazinyl)butyl)-6-methyl-1,2,4-benzothiadiazin-3(4H)one 1,1-dioxide, 2-(3-(4-(2-pyrimidinyl)-1-piperazinyl)propyl)-4-methyl-7-methoxy-1,2,4-benzothiadiazin-3(4H)one 1,1-dioxide, 2-(3-(4-(2-pyrimidinyl)-1-piperazinyl)propyl)-7-chloro-4-methyl-1,2,4-benzothiadiazin-3(4H)one 1,1-dioxide, 2-(3-(4-(2-pyrimidinyl)-1-piperazinyl)propyl)-6-acetylamino-1,2,4-benzothiadiazin-3(4H)one 1,1-dioxide, 2-(3-(4-(2-pyrimidinyl)-1-piperazinyl)propyl)-6-trifluoromethyl-1,2,4-benzothiadiazin-3(4H)one 1,1-dioxide, 2-(4-(4-(2-pyrimidinyl)-1-piperazinyl)butyl)-6-trifluoromethyl-1,2,4-benzothiadiazin-3(4H)one 1,1-dioxide, 2-(3-(4-(2-pyrimidinyl)-1-piperazinyl)propyl)-6,8-dichloro-1,2,4-benzothiadiazin-3(4H)one 1,1-dioxide, 2-(3-(4-(2-pyrimidinyl)-1-piperazinyl)propyl)-6,8-dichloro-4-methyl-1,2,4-benzothiadiazin-3(4H)one 1,1-dioxide, 2-(3-(4-(2-pyrimidinyl)-1-piperazinyl)propyl)-6,7-dichloro-1,2,4-benzothiadiazin-3(4H)one 1,1-dioxide, 2-(3-(4-(2-pyrimidinyl)-1-piperazinyl)propyl)-6,7-dichloro-4-methyl-1,2,4-benzothiadiazin-3(4H)one 1,1-dioxide, 2-(3-(4-(2-pyrimidinyl)-1-piperazinyl)propyl)-6-chloro-7-methyl-1,2,4-benzothiadiazin-3(4H)one 1,1-dioxide, 2-(4-(4-(2-pyrimidinyl)-1-piperazinyl)butyl)-6-chloro-7-methyl-1,2,4-benzothiadiazin-3(4H)one 1,1-dioxide, 2-(3-(4-(2-pyrimidinyl)-1-piperazinyl)propyl)-5,7-dichloro-1,2,4-benzothiadiazin-3(4H)one 1,1-dioxide, 2-(4-(4-(2-pyrimidinyl)-1-piperazinyl)butyl)-5,7-dichloro-1,2,4-benzothiadiazin-3(4H)one 1,1-dioxide, 2-(3-(4-(2-pyrimidinyl)-1-piperazinyl)propyl)-7-nitro-1,2,4-benzothiadiazin-3(4H)one 1,1-dioxide, 2-(4-(4-(2-pyrimidinyl)-1-piperazinyl)butyl)-7-nitro-1,2,4-benzothiadiazin-3(4H)one 1,1-dioxide, 2-(3-(4-(2-pyrimidinyl)-1-piperazinyl)propyl)-7-nitro-4-methyl-1,2,4-benzothiadiazin-3(4H)one 1,1-dioxide, 2-(3-(4-(2-pyrimidinyl)-1-piperazinyl)propyl)-6-chloro-1,2,4-benzothiadiazin-3(4H)one 1,1-dioxide, 2-(3-(4-(2-pyrimidinyl)-1-piperazinyl)propyl)-7-methoxy-1,2,4-benzothiadiazin-3(4H)one 1,1-dioxide, 2-(3-(4-(2-pyrimidinyl)-1-piperazinyl)propyl)-7-amino-1,2,4-benzothiadiazin-3(4H)one 1,1-dioxide, 2-(3-(4-(2-pyrimidinyl)-1-piperazinyl)propyl)-7-amino-4-methyl-1,2,4-benzothiadiazin-3(4H)one 1,1-dioxide, 2-(3-(4-(2-pyrimidinyl)-1-piperazinyl)propyl)-7-acetylamino-4-methyl-1,2,4-benzothiadiazin-3(4H)one 1,1-dioxide, 2-(3-(4-(2-pyrimidinyl)-1-piperazinyl)propyl)-7-ethoxycarbonylamino-4-methyl-1,2,4-benzothiadiazin-3(4H)one 1,1-dioxide, 2-(3-(4-(2-pyrimidinyl)-1-piperazinyl)propyl)-7-trifluoromethyl-1,2,4-benzothiadiazin-3(4H)one 1,1-dioxide, 2-(4-(4-(2-pyrimidinyl)-1-piperazinyl)butyl)-7-trifluoromethyl-1,2,4-benzothiadiazin-3(4H)one 1,1-dioxide, 2-(4-(4-(5-phenyl-2-pyrimidinyl)-1-piperazinyl)butyl)isoindole-1,3-(2H)dione, 2-(4-(4-(5-(3,4-dimethoxyphenyl)-2-pyrimidinyl)-1-piperazinyl)butyl)isoindole-1,3(2H)dione, 2-(4-(4-(5-(2-chloro-6-fluorophenyl)-2-pyrimidinyl)-1-piperazinyl)butyl)isoindole-1,3(2H)dione, 2-(4-(4-(2-pyrimidinyl)-1-piperazinyl)butyl)isoindole-1,3(2H)dione, 2-(4-(4-(5-fluoro-2-pyrimidinyl)-1-piperazinyl)butyl)isoindole-1,3-(2H)dione, 2-(4-(4-(5-(4-chlorophenyl)-2-pyrimidinyl)-1-piperazinyl)butyl)isoindole-1,3(2H)dione, 2-(4-(4-(5-(4-chlorophenyl)-2-pyrimidinyl)-1-piperazinyl)butyl)isoindole-1,3(2H)dione, 2-(3-(4-(5-(4-chlorophenyl)-2-pyrimidinyl)-1-piperazinyl)propyl)isoindole-1,3(2H)dione, 2-(2-(4-(5-(4-chlorophenyl)-2-pyrimidinyl)-1-piperazinyl)ethyl)isoindole-1,3(2H)dione, 2-(3-(4-(2-pyrimidinyl)-1-piperazinyl)propyl)isoindole-1,3(2H)dione, 2-(2-(4-(2-pyrimidinyl)-1-piperazinyl)ethyl)isoindole-1,3(2H)dione, 2-(3-(4-(5-phenyl-2-pyrimidinyl)-1-piperazinyl)propyl)isoindole-1,3(2H)dione, 2-(2-(4-(5-(phenyl-2-pyrimidinyl)-1-piperazinyl)ethyl)isoindole-1,3(2H)dione, 2-(3-(4-(2-pyrimidinyl)-1-piperazinyl)-2-hydroxypropyl)isoindole-1,3(2H)dione, 2-(3-(4-(5-(4-chlorophenyl)-2-pyrimidinyl)-1-piperazinyl)-2-hydroxypropyl)isoindole-1,3(2H)dione, 2-(3-(4-(5-(4-methoxyphenyl)-2-pyrimidinyl)-1-piperazinyl)-2-hydroxypropyl)isoindole-1,3(2H)dione, 2-(3-(4-(5-(3-trifluoromethylphenyl)-2-pyrimidinyl)-1-piperazinyl)-2-hydroxypropyl)isoindole-1,3(2H)dione, 2-(4-(4-(2-pyrimidinyl)-1-piperazinyl)butyl)-5,6-dichloroisoindole-1,3-(2H)dione, 2-(4-(4-(5-phenyl-2-pyrimidinyl)-1-piperazinyl)butyl)-5,6-dichloroisoindole-1,3(2H)dione, 2-(4-(4-(2-pyrimidinyl)-1-piperazinyl)butyl)-5-nitroisoindole-1,3-(2H)dione, 2-(4-(4-(5-phenyl-2-pyrimidinyl)-1-piperazinyl)butyl)-5-nitroisoindole-1,3(2H)dione, 2-(4-(4-(2-pyrimidinyl)-1-piperazinyl)butyl)-4-nitroisoindole-1,3(2H)dione, 2-(4-(4-(5-(4-chlorophenyl)-2-pyrimidinyl)-1-piperazinyl)butyl)-4-nitroisoindole-1,3(2H)dione, 2-(4-(4-(5-phenyl-2-pyrimidinyl)-1-piperazinyl)butyl)-5-aminoisoindole-1,3(2H)dione, 2-(4-(4-(5-phenyl-2-pyrimidinyl)-1-piperazinyl)butyl)-5-acetylaminoisoindole-1,3(2H)dione, 2-(4-(4-(5-phenyl-2-pyrimidinyl)-1-piperazinyl)butyl)-4-aminoisoindole-1,3(2H)dione, 2-(4-(4-(5-(3-indolyl)-2-pyrimidinyl)-1-piperazinyl)butyl)isoindole-1,3(2H)dione, 2-(4-(4-(5-phenyl-2-pyrimidinyl)-1-piperazinyl)butyl)-5-methylisoindole-1,3(2H)dione, 2-(4-(4-(5-phenyl-2-pyrimidinyl)-1-piperazinyl)butyl)-4-methoxyisoindole-1,3(2H)dione and 2-(4-(4-(5-phenyl-2-pyrimidinyl)-1-piperazinyl)butyl)-5-trifluoromethylisoindole-1,3(2H)dione.

The psychotropic properties of the substances according to the invention were investigated as follows, for example:

1. Amphetamine potentiation

Substances having antidepressant effects potentiate the amphetamine-induced stereotypic behaviour of the rat. The $ED_{50}$ value which is given is the dose at which the behaviour induced after i.v. administration of 2 mg/kg DL-amphetamine sulphate is potentiated by 50%. Lit.: J. L. Howard et al., in: Antidepressants: Neurochemical, Behavioral and Clinical Perspectives, edited by S. J. Enna et al., Raven Press, New York, pages 107–120, 1981.

The following examples may be preferably mentioned in this context:

| Substance | $ED_{50}$ (mg/kg i.p.) |
|---|---|
| Example | |
| 1 | 18 |
| 4 | 3 |
| 8 | 1 |
| 20 | 5 |

| Substance | ED$_{50}$ (mg/kg i.p.) |
|---|---|
| 49 | 3 |
| 50 | 3 |
| 54 | 0.4 |
| 60 | 16 |
| 61 | 5 |
| 64 | 2 |

2. Tetrabenazine antagonism

Antidepressants antagonise the ptosis induced by tetrabenazine in mice. The ED$_{50}$ value indicates the dose at which the ptosis induced by tetrabenazine (20 mg/kg i.p.) is reduced to 50%.

Lit.: J. L. Howard et al., in: Antidepressants: Neuochemical, Behavioral and Clinical Perspectives, edited by S. J. Enna et al., Raven Press, New York, pages 117–120, 1981.

The following examples may be preferably mentioned in this context:

| Substance | ED$_{50}$ (mg/kg i.p.) |
|---|---|
| Example | |
| 6 | 40 |
| 18 | 21 |
| 60 | 5 |
| 64 | 18 |

3. Behavioral Despair

When placed in a glass cylinder filled with water, rats initially show vigorous swimming movements which alternate with phases of immobility which increase in length. Many antidepressants of a variety of chemical structures shorten the duration of this immobility. The ED$_{50}$ value indicates the dose of a test substance at which the immobility during the period of the experiment is reduced by 50%.

Lit.: R. D. Porsolt et al., Europ. J. Pharmacol. 47, 379–391, 1978.

The following examples may be preferably mentioned in this context:

| Substance | ED$_{50}$ (mg/kg i.p.) |
|---|---|
| Example | |
| 4 | 12 |
| 8 | 33 |
| 12 | 50 |
| 54 | 20 |

4. Tedeschi test

In mice, anxiolytics bring about a reduction in the shock-induced aggressive behaviour. The ED$_{50}$ value indicates the dose at which the aggressive behaviour is reduced by 50% within the period of the experiment. Lit.: Tedeschi et al., J. Pharmacol. Exp. Ther. 129, 28–34, 1954.

The following examples may be preferably mentioned in this context:

| Substance | ED$_{50}$ (mg/kg i.p.) |
|---|---|
| Example | |
| 4 | 20 |
| 6 | 15 |
| 7 | 5 |
| 8 | 12 |
| 12 | 16 |
| 15 | 6 |
| 18 | 9 |
| 50 | 32 |
| 54 | 10 |

5. Passive avoidance behaviour

After entering a darkened box, rats receive an electric shock and thus avoid reentering the box. Rats under the influence of anxiolytics enter the box in spite of having experienced the shock. The time up to entry into the box is timed with a stopwatch. The minimum effective dose (MED) in mg/kg is reported. Lit.: Ader et al., Psychon. Sci. 26, 125–128, 1972.

The following examples may be preferably mentioned in this context:

| Substance | MED (mg/kg i.p.) |
|---|---|
| Example | |
| 4 | 1 |
| 7 | 0.5 |
| 10 | 1 |
| 11 | 1 |
| 18 | 1 |
| 54 | 5 |

6. Serotonin receptor

The direct or indirect effect on the serotonergic system by, for example, anxiolytic, tranquillising, neuroleptic or antidepressant active compounds is known. Substances according to the invention interact specifically with serotonin receptors from calf hippocampus. The concentration at which 50% of the $^3$H-serotonin employed is displaced is reported (K$_i$ values). Lit.: Peroutka, S. J. and S. H. Snyder, Molec. Pharmacol. 16, 687, 1979.

The following may be preferably mentioned as examples:

| Substance | K$_i$ (nM) |
|---|---|
| Example | |
| 1 | 10 |
| 7 | 20 |
| 10 | 14 |
| 11 | 30 |
| 19 | 30 |
| 24 | 20 |
| 32 | 10 |
| 33 | 60 |
| 36 | 9 |
| 37 | 80 |

The abovementioned examples of activity are intended to illustrate the invention and make it clear, without restricting it to these examples.

The present invention includes pharmaceutical preparations which, in addition to non-toxic, inert pharmaceutically suitable vehicles, contain one or more compounds according to the invention or their salts, or which consist of one or more compounds according to the invention or their salts, and processes for the production of these preparations.

The present invention also includes pharmaceutical preparations in dosage units. This means that the preparations are in the form of individual parts, for example tablets, coated tablets, capsules, pills, suppositories and ampoules, of which the content of active compound corresponds to a fraction or a multiple of an individual dose. The dosage units can contain, for example, 1, 2, 3 or 4 individual doses of ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable vehicles, there are to be understood solid, semi-solid or liquid diluents, fillers and formulation auxiliaries of all kinds.

Tablets, coated tablets, capsules, pills, granules, suppositories, solutions, suspensions and emulsions may be mentioned as preferred pharmaceutical preparations.

Tablets, coated tablets, capsules, pills and granules can contain the active compound or compounds alongside the customary vehicles such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerine, (d) disintegrating agents, for example agar-agar, calcium carbonate and sodium bicarbonate, (e) solution retarders, for example paraffin, and (f) absorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned vehicles, can also be in a micro-encapsulated form.

Suppositories can contain, in addition to the active compound or compounds, the customary water-soluble or water-insoluble vehicles, for example polyethylene glycols, fats, for example cacao fat, and higher esters (for example $C_{14}$-alcohol with $C_{16}$-fatty acid) or mixtures of these substances.

Solutions and emulsions can contain the customary vehicles in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerine, glycerine-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary vehicles in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminium metahydroxide, bentonide, agar-agar and tragacanth or mixtures of these substances.

The formulation forms mentioned can also contain dyestuffs, preservatives and additives which improve the odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutical active compounds in addition to the compounds of the formula (I) and/or their salts.

The abovementioned pharmaceutical preparations are manufactured in the usual manner according to known methods, for example by mixing the active compound or the active compounds with the vehicle or vehicles.

The present invention also includes the use of the compounds of the formula (I) and/or their salts and of pharmaceutical preparations which contain one or more compounds of the formula (I) and/or their salts in human medicine for the prevention, amelioration and/or cure of the abovementioned illnesses.

The active compounds of the pharmaceutical preparations can preferably be administered orally, parenterally and/or rectally, preferably orally and parenterally, especially orally and intravenously.

In general, it has proved advantageous to administer the active compound or compounds in amounts of about 0.01 to about 10, preferably 0.1 to 1, mg/kg of body weight every 24 hours on parenteral (i.v. or i.m.) administration, and in amounts of about 0.05 to about 100, preferably 0.1 to 10, mg/kg of body weight every 24 hours on oral administration, optionally in the form of several individual administrations, in order to achieve the desired results. An individual administration contains the active compound or the active compounds preferably in amounts of about 0.01 to about 30, especially 0.03 to 3, mg/kg of body weight.

However, it can be necessary to deviate from the dosages mentioned and in particular to do so as a function of the nature and body weight of the subject to be treated, the nature and severity of the illness, the nature of the preparation and of the administration of the medicine, and the time or interval over which the administration takes place. Thus it can suffice in some cases to manage with less than the abovementioned amount of active compound, whilst in other cases the above-mentioned amount of active compound must be exceeded. The particular required optimum dosage and the type of administration of the active compounds can easily be decided by anyone skilled in the art, on the basis of his expert knowledge.

The present invention is to be illustrated in more detail by the examples which follow:

EXAMPLE 1

Preparation of
(2-(4-(4-(2-pyrimidinyl)-1-piperazinyl)butyl)isoindole-1,3(2H)dione

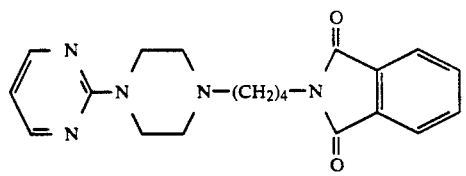

0.2 mol of 2-(4-bromobutyl)isoindole-1,3(2H)dione and 0.2 mol of 1-(2-pyrimidyl)piperazine are stirred with 0.2 mol of $K_2CO_3$ at 120°–130° C. under an atmosphere of $N_2$ overnight. The mixture is then evaporated to dryness. Water is added and the residue is taken up in methylene chloride. After drying the organic solution, it is evaporated to obtain an oil which crystallises on trituration with cyclohexane.

Yield: 96% of theory; melting point = 138° C.

The following were prepared analogously:

EXAMPLE 4

Preparation of
2-(4-(4-(5-phenyl-2-pyrimidinyl)-1-piperazinyl)butyl)isoindole-1,3(2H)dione

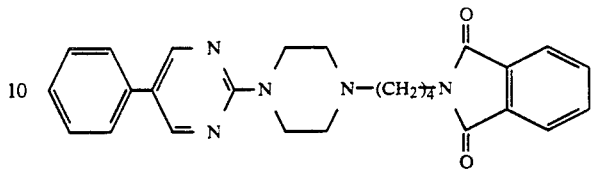

0.05 mol of 2-(4-bromobutyl)isoindole-1,3(2H)dione and 0.05 mol of 1-(5-phenyl-2-pyrimidinyl)piperazine are heated, with stirring, with 0.05 mol of $K_2CO_3$ in 80 ml of chlorobenzene under an atmosphere of $N_2$ for 8 hours. After cooling, the mixture is evaporated to dryness in a rotary evaporator. Water is added to the residue which is taken up in methylene chloride. The dried methylene chloride solution is applied to a column of silica gel and eluted with $CH_2Cl_2$/isopropanol (10:1). The substance is then recrystallised.

| Example No. | Formula | m.p. (°C.) | Yield, % of theory |
|---|---|---|---|
| 2 | 2-(2-(4-(2-Pyrimidinyl)-1-piperazinyl)ethyl)isoindole-1,3(2H)dione | 124° (from cyclohexane) | 45 |
| 3 | 2-(3-(4-(2-Pyrimidinyl)-1-piperazinyl)propyl)isoindole-1,3(2H)dione | 95° (from cyclohexane) | 46 |

Yield: 88% of theory; melting point: 126° C. (from cyclohexane)

The following were prepared analogously:

| Example No. | Formula | m.p. (°C.) | Yield, % of theory |
|---|---|---|---|
| 5 | 2-(2-(4-(5-Phenyl-2-pyrimidinyl)-1-piperazinyl)ethylisoindole-1,3(2H)dione | 178° | 49 |
| 6 | 2-(3-(4-(5-Phenyl-2-pyrimidinyl)-1-piperazinyl)propyl)isoindole-1,3(2H)dione | 148° | 62 |

2-(4-(4-(2-Pyrimidinyl)-1-piperazinyl)butyl)-1,2-benzisothiazol-3(2H)one 1,1-dioxide -continued

| Example No. | Formula | m.p. (°C.) | Yield, % of theory |
|---|---|---|---|
| 7 | | 137–138° (from isopropanol) hydrochloride: 221–222° | 53 |
| 8 | 2-(4-(4-(5-(2-Chloro-6-fluorophenyl)-2-pyrimidinyl)-1-piperazinyl)butyl)-isoindole-1,3(2H)dione | 123–124° | 82 |
| 9 | 2-(4-(4-(5-Phenyl-2-pyrimidinyl)-1-piperazinyl)butyl)-1,2-benzisothiazol-3(2H)one 1,1-dioxide | 253° (from ethanol) | 65.5 |
| 10 | 2-(4-(4-(2-Pyrimidinyl)-1-piperazinyl)butyl-5-chloro-1,2-benzisothiazol-3(2H)one 1,1-dioxide | 120–121° (from isopropanol) | 30 |
| 11 | 2-(4-(4-(2-Pyrimidinyl)-1-piperazinyl)butyl)-6-chloro-1,2-benzisothiazol-3(2H)one 1,1-dioxide | 154–155° (from isopropanol) | 34 |
| 12 | 2-(4-(4-5-(3,4-Dimethoxyphenyl)-2-pyrimidinyl)-1-piperazinyl)butyl)-isoindole-1,3(2H)dione | 160–170° (from ethyl acetate) | 89 |
| 13 | 2-(4-(4-(5-(4-Chlorophenyl)-2-pyrimidinyl)-1-piperazinyl)butyl)isoindole-1,3(2H)dione | 192–193° | 70 |
| 14 | 2-(3-(4-(5-(4-Chlorophenyl)-2-pyrimidinyl)-1-piperazinyl)propyl)isoindole-1,3(2H)dione | 174–175° | 56 |

| Example No. | Formula | m.p. (°C.) | Yield, % of theory |
|---|---|---|---|
| 15 | 2-(2-(4-(5-(4-Chlorophenyl)-2-pyrimidinyl)-1-piperazinyl)ethyl)isoindole-1,3(2H)dione<br>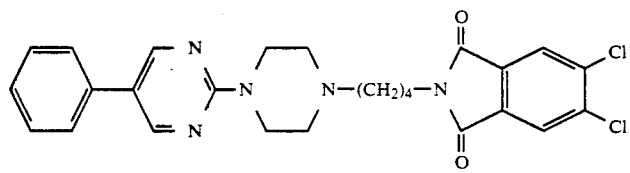 | 209-210° | 52 |
| 16 | 2-(4-(4-(5-(3-Indolyl)-2-pyrimidinyl)-1-piperazinyl)butyl)isoindole-1,3(2H)dione<br>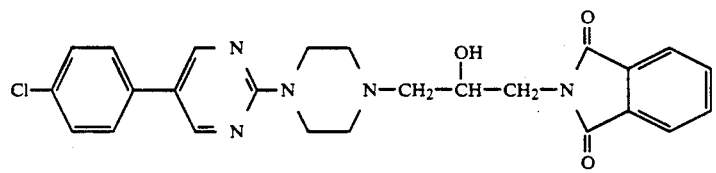 | 163-164° | 66 |

EXAMPLE 17

Preparation of 2-(4-(4-(5-phenyl-2-pyrimidinyl)-1-piperazinyl)butyl)-5,6-dichloroisoindole-1,3(2H)dione

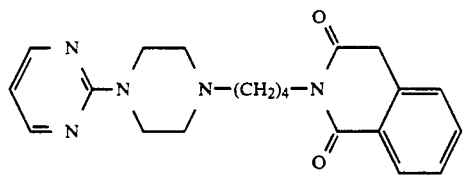

0.005 mol of 4,5-dichlorophthalic anhydride and 0.005 mol of 1-(4-aminobutyl)-4-(5-phenyl-2-pyrimidinyl)piperazine in 20 ml of absolute pyridine are boiled under reflux, under an atmosphere of $N_2$, for several hours. After cooling, the product which has crystallised out is filtered off and washed with isopropyl ether.

Yield: 90% of theory; melting point: 206°-207° C.

EXAMPLE 18

Preparation of 2-(3-(4-(5-(4-chlorophenyl)-2-pyrimidinyl)-1-piperazinyl)-2-hydroxypropyl)isoindole-1,3(2H)dione 0.022 mol of 2-(2,3-epoxypropyl)isoindole-1,3(2H)dione, 0.02 mol of 1-(5-(4-chlorophenyl)-2-pyrimidinyl)piperazine and 70 ml of isopropanol are heated to boiling for 2 hours. The mixture is evaporated and the residue is purified by column chromatography on silica gel 60. After elution with methylene chloride-/alcohol (96:4), the compound is stirred with alcohol and filtered off with suction.

Melting point = 180°-181° C., yield: 88% of theory

EXAMPLE 19

Preparation of 2-(4-(4-(2-pyrimidinyl)-1-piperazinyl)butyl)isoquinoline-1,3(2H, 4H)dione 0.02 mol of 2-benzopyran-1,3(4H)dione and 0.02 mol of 1-(4-aminobutyl)-4-(2-pyrimidinyl)piperazine are heated at 160°-170° C. for 1 hour under an atmosphere of $N_2$, with stirring. The mixture is then allowed to cool and the substance is dissolved in methylene chloride. The substance is purified over a silica gel column (mobile phase: $CH_2Cl_2$/iprOH (10:0.5)).

Yield: 33% of theory; melting point: 103°-104° C.

The following were prepared analogously:

| Example No. | Formula | m.p. (°C.) | Yield, % of theory |
|---|---|---|---|
| 20 | 2-(4-(4-(5-(3,4-Dimethoxyphyenyl)-2-pyrimidinyl)-1-piperazinyl)butyl)-isoquinoline-1,3(2H,4H)dione | 179–187° | 51 |
| 21 | 2-(4-(4-(5-Phenyl-2-pyrimidinyl)-1-piperazinyl)butyl)isoindole-1,3(2H)dione | 126° | 60 |

EXAMPLE 22

Preparation of 2-(4-(4-(2-pyrimidinyl)-1-piperazinyl)butyl)-5-fluoro-1,2-benzisothiazol-3(2H)one 1,1-dioxide

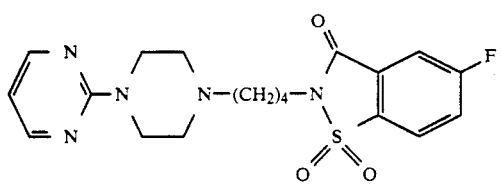

0.02 mol of 5-fluoro-2-(4-bromobutyl)-1,2-benzisothiazol-3(2H)one 1,1-dioxide and 0.02 mol of 1-(2-pyrimidinyl)piperazine are stirred with 0.02 mol of $K_2CO_3$ in 150 ml of absolute DMF at 100° C. for 1 hour. The mixture is then evaporated. Water is added and the organic substance is taken up in methylene chloride. The dried $CH_2Cl_2$ phase is applied to a silica gel column and eluted with $CH_2Cl_2/CH_3OH$ (95:5).

Yield: 34% of theory; melting point: 138°–139° C.

The following were prepared analogously:

| Example No. | Formula | m.p. (°C.) | Yield, % of theory |
|---|---|---|---|
| 23 | 2-(4-(4-(5-Iodo-2-pyrimidinyl)-1-piperazinyl)butyl)-1,2-benzisothiazol-3(2H)one 1,1-dioxide | 124–125° | 40 |
| 24 | 2-(4-(4-(2-Pyrimidinyl)-1-piperazinyl)butyl)-6-nitro-1,2-benzisothiazol-3(2H)one 1,1-dioxide | 168° | 45 |
| 25 | 2-(3-(4-(2-Pyrimidinyl)-1-piperazinyl)propyl)-1,2-benzisothiazol-3(2H)one 1,1-dioxide | 131° | 50 |

2-(4-(4-(5-Fluoro-2-pyrimidinyl)-1-piperazinyl)butyl)-1,2-benzisothiazol-3(2H)one 1,1-dioxide -continued

| Example No. | Formula | m.p. (°C.) | Yield, % of theory |
|---|---|---|---|
| 26 | (structure with fluoropyrimidinyl-piperazinyl-butyl-benzisothiazol-dioxide) | 124–125° | 40 |
| 27 | 2-(4-(4-(5-(3-Trifluoromethylphenyl)-2-pyrimidinyl)-1-piperazinyl)butyl)-1,2-benzisothiazol-3(2H)one 1,1-dioxide (structure) | 144–145° | 40 |

EXAMPLE 28

Preparation of 3-(4-(4-(2-pyrimidinyl)-1-piperazinyl)butyl)quinazoline-2,4(1H,3H)dione

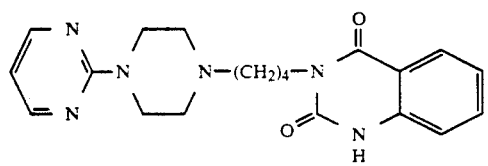

A solution of 0.028 mol of phosgene in 20 ml of absolute toluene is added, with stirring, to 0.02 mol of N-(4-(4-(2-pyrimidinyl)-1-piperazinyl)butyl)-2-aminobenzamide, 0.04 mol of triethylamine and 80 ml of absolute toluene. After the exothermic reaction has abated, the mixture is stirred for 2 hours. It is evaporated and the residue is shaken with methylene chloride and dilute aqueous ammonia. The solvent is removed from the organic phase and the residue is recrystallised.

Melting point: 187°–188° C. (from ethyl acetate)
Yield: 59% of theory
The following were prepared analogously:

| Example No. | Formula | m.p. (°C.) | Yield, % of theory |
|---|---|---|---|
| 29 | 3-(3-(4-(2-Pyrimidinyl)-1-piperazinyl)propyl)quinazoline-2,4(1H,3H)dione (structure) | 177–178° C. (from ethyl acetate) | 74 |
| 30 | 3-(4-(4-(2-Pyrimidinyl)-1-piperazinyl)butyl)-6-chloroquinazoline-2,4(1H,3H)-dione (structure) | 181–182° (from ethyl acetate) | 44 |
| 31 | 3-(3-(4-(2-Pyrimidinyl)-1-piperazinyl)propyl)-6-chloroquinazoline-2,4(1H,3H)-dione (structure) | 245–246° (from DMF) | 76 |
| 32 | 2-(3-(4-(2-Pyrimidinyl)-1-piperazinyl)propyl)1,2,4-benzothiadiazin-3(4H)one 1,1-dioxide (structure) | 182.4° (from ethyl acetate) | 93 |

| Example No. | Formula | m.p. (°C.) | Yield, % of theory |
|---|---|---|---|
| 33 | 2-(4-(4-(2-Pyrimidinyl)-1-piperazinyl)butyl)-1,2,4-benzothiadiazin-3(4H)one 1,1-dioxide<br>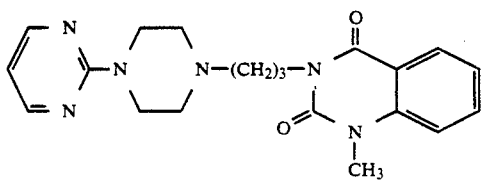 | 131.6°<br>(from isopropanol) | 83 |

EXAMPLE 34

Preparation of 3-(3-(4-(2-pyrimidinyl)-1-piperazinyl)propyl)-1-methyl-quinazoline-2,4(1H,3H)dione

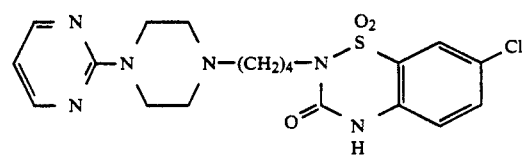

0.02 mol of 3-(3-(4-(2-pyrimidinyl)-1-piperazinyl)propyl)quinazoline-2,4(1H,3H)dione is added to 100 ml of absolute DMF, 0.02 mol of sodium hydride (55-60% strength dispersion) is added and the mixture is stirred for 1 hour. After adding 0.02 mol of methyl iodide, the mixture is stirred for a further 3 hours, poured into 300 ml of water and extracted by shaking with methylene chloride. The organic phase is evaporated and the residue is purified by column chromatography over silica gel 60. After elution with methylene chloride/methanol (95:5), the compound is recrystallised.

Melting point: 158°-159° (from ethyl acetate),
Yield: 77% of theory
The following were prepared analogously:

EXAMPLE 38

Preparation of 2-(4-(4-(2-pyrimidinyl)-1-piperazinyl)butyl)-7-chloro-1,2,4-benzothiodiazin-3(4H)one 1,1-dioxide 0.01 mol of 7-chloro-2-(4-bromobutyl)-1,2,4-benzothiadiazin-3(4H)one 1,1-dioxide is dissolved in 50 ml of DMF, 0.013 mol of 1-(2-pyrimidinyl)piperazine is added and the mixture is heated at 100° C. for 1 hour. It is then evaporated and the residue purified over silica gel 60. Mobile phase: $CH_2Cl_2$/MeOH (95:5).

Yield: 43% of theory, melting point: 129° C.

| Example No. | Formula | m.p. (°C.) | Yield, % of theory |
|---|---|---|---|
| 35 | 3-(4-(4-(2-Pyrimidinyl)-1-piperazinyl)butyl)-6-chloro-1-methylquinazoline-2,4(1H,3H)dione | 148-149°<br>(from ethyl acetate) | 76 |
| 36 | 2-(3-(4-(2-Pyrimidinyl)-1-piperazinyl)propyl)-4-methyl-1,2,4-benzothiadiazin-3(4H)one 1,1-dioxide | 121.7°<br>(from isopropanol) | 58 |
| 37 | 2-(4-(4-(2-Pyrimidinyl)-1-piperazinyl)butyl)-4-methyl-1,2,4-benzothiadiazin-3(4H)one 1,1-dioxide | 131.6°<br>(from isopropanol) | 70 |

EXAMPLE 39

Preparation of
N-(3-(4-(2-pyrimidinyl)-1-piperazinyl)propyl)-2-aminobenzamide

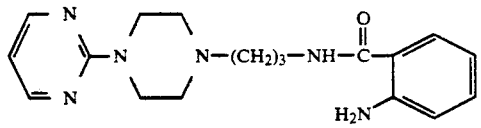

0.02 mol of 1-(3-aminopropyl)-4-(2-pyrimidinyl)piperazine is dissolved in 100 ml of absolute dimethylformamide, 0.02 mol of isatoic anhydride is added, and the mixture is stirred for 1 hour. It is diluted with 50 ml of water, shaken with ethyl acetate and the organic phase is evaporated. Purification is by column chromatography over silica gel 60. After elution with methylene chloride/methanol 93:7, the resulting oil can be crystallised from ethyl acetate with isopropyl ether.

Melting point: 79°–80° C.,
Yield: 80% of theory
The following were prepared analogously:

EXAMPLE 45

Preparation of
N-(4-(4-(2-pyrimidinyl)-1-piperazinyl)butyl)-2-nitrobenzenesulphonamide

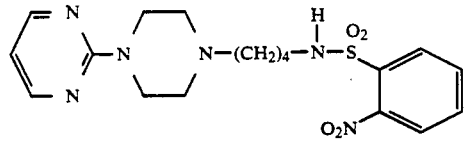

0.1 mol of 1-(4-aminobutyl)-4-(2-pyrimidinyl)piperazine is dissolved in 150 ml of toluene, 100 ml of 20% strength NaOH are added and, with vigorous stirring and cooling in ice, 0.1 mol of 2-nitrobenzenesulphonyl chloride, dissolved in 150 ml of toluene, is added dropwise within 20 minutes.

The mixture is stirred at room temperature for 2 hours, acidified with 2N HCl and the toluene is separated off. The aqueous phase is made alkaline with ammonia, extracted by shaking with ethyl acetate, and the

| Example No. | Formula | m.p. (°C.) | Yield, % of theory |
|---|---|---|---|
| 40 | N-(4-(4-(2-Pyrimidinyl)-1-piperazinyl)butyl)-2-aminobenzamide | 113–114° (from ethyl acetate/ isopropanol ether) | 80 |
| 41 | N-(3-(4-(2-Pyrimidinyl)-1-piperazinyl)propyl)-2-amino-5-chlorobenzamide | 119–120° (from ethyl acetate/ isopropyl ether) | 76 |
| 42 | N-(4-(4-(2-Pyrimidinyl)-1-piperazinyl)butyl)-2-amino-5-chlorobenzamide | 118–119° (from ethyl acetate) | 63 |
| 43 | N-(3-(4-(2-Pyrimidinyl)-1-piperazinyl)propyl)-2-methylaminobenzamide | 102–103° (from ethyl acetate/ isopropyl ether) | 77 |
| 44 | N-(4-(4-(2-Pyrimidinyl)-1-piperazinyl)butyl)-2-methylaminobenzamide | 214–215° (dihydrochloride) | 65 | organic phase is evaporated. The residue is crystallised from ethyl acetate and isopropyl ether.

Yield: 77% of theory, melting point: 102.3° C.

The following was prepared analogously:

| Example No. | Formula | m.p. (°C.) | Yield, % of theory |
|---|---|---|---|
| 46 | N-(3-(4-(2-Pyrimidinyl)-1-piperazinyl)propyl)-2-nitrobenzenesulphonamide 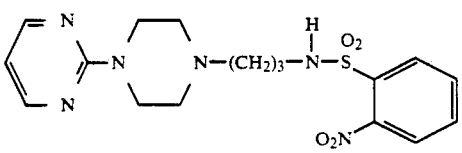 | 121.7° | 78 |

EXAMPLE 47

Preparation of N-(4-(4-(2-pyrimidinyl)-1-piperazinyl)butyl)-2-aminobenzenesulphonamide

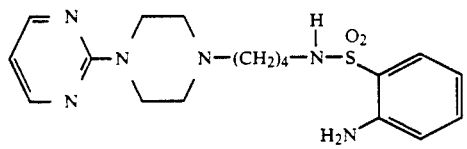

0.06 mol of N-(4-(4-(2-pyrimidinyl)-1-piperazinyl)-butyl)-2-nitrobenzenesulphonamide is dissolved in 500 ml of MeOH, 2.4 g of 5% Pd-C are added, the mixture is heated to boiling and 0.17 mol of hydrazine hydrate in 50 ml of MeOH is added dropwise within 15 minutes. After boiling for a further 30 minutes, the mixture is filtered, the filtrate is evaporated, the residue is taken up in diethyl ether, washed with water, evaporated again and crystallised from isorpopanol/isopropyl ether.

Yield: 86% of theory; melting point: 82° C.

The following was prepared analogously:

EXAMPLE 49

Preparation of 1-(4-aminobutyl)-4-(5-phenyl-2-pyrimidinyl)piperazine

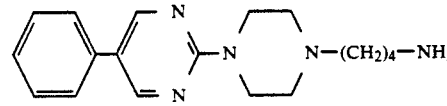

0.005 mol of 2-(4-(4-(5-phenyl-2-pyrimidinyl)-1-piperazinyl)butyl)isoindole-1,3(2H)dione and 0.005 mol of hydrazine hydrate in 25 ml of ethanol and 0.6 ml of $H_2O$ are stirred at 60° to 70° C. under an atmosphere of $N_2$ for 7 hours. After cooling, the mixture is acidified with 7.5 ml of 2N HCl, and diluted with 100 ml of $H_2O$. The insoluble white product (hydrazide) is filtered off and the solution is evaporated. The remaining solids are shaken and extracted with methylene chloride/2N NaOH. After drying the organic phase, it is evaporated. The semi-crystalline residue is triturated and crystallised with isopropyl ether. It is recrystallised from cyclohexane.

Yield: 67% of theory; melting point: 66°-67° C., dihydrochloride: melting point > 250° C. (decomposition)

The following were prepared analogously:

| Example No. | Formula | m.p. (°C.) | Yield, % of theory |
|---|---|---|---|
| 48 | N-(3-(4-(2-Pyrimidinyl)-1-piperazinyl)propyl)-2-aminobenzenesulphonamide 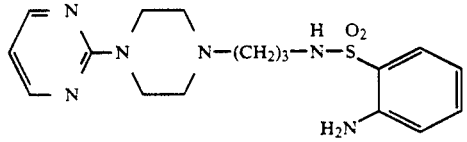 | 61.4° | 86 |

| Example No. | Formula | m.p. (°C.) | Yield, % of theory |
|---|---|---|---|
| 50 | 1-(4-Aminobutyl)-4-(5-(2-fluoro-6-chlorophenyl)-2-pyrimidinyl)piperazine 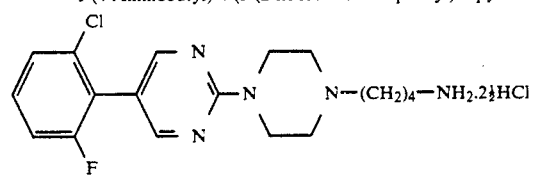 | 275° (decomposition) | 93 |
| | 1-(4-Aminobutyl)-4-(5-(3,4-dimethoxyphenyl)-2-pyrimidinyl)piperazine | | |

| Example No. | Formula | m.p. (°C.) | Yield, % of theory |
|---|---|---|---|
| 51 | H₃C—O—[3,4-dimethoxyphenyl]-CH=CH-pyrimidinyl-piperazine-N—(CH₂)₄—NH₂·2HCl | 94–95° (base) 273–275° (decomposition) | 79 |
| | 1-(3-Aminopropyl)-4-(5-(4-chlorophenyl)-2-pyrimidinyl)piperazine | | |
| 52 | Cl-phenyl-pyrimidinyl-piperazine-N—(CH₂)₃—NH₂ | 103–104° | 80 |
| | 1-(4-Aminobutyl)-4-(5-(3-indolyl)-2-pyrimidinyl)piperazine | | |
| 53 | HN-indolyl-pyrimidinyl-piperazine-N—(CH₂)₄—NH₂ | 137–138° | 67 |

EXAMPLE 54

Preparation of ethyl 4-(5-phenyl-2-pyrimidinyl)-1-piperazinecarboxylate

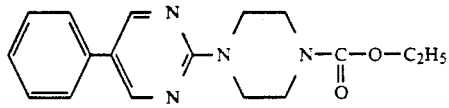

50 ml of 2N NaOCH₃ solution are added to 0.1 mol of ethyl 4-(aminoiminomethyl)-1-piperazinecarboxylate and 0.1 mol of N-(3-dimethylamino-2-(phenyl)-2-propenylidene)-N-methylmethaniminium perchlorate in 400 ml of CH₃OH. After half an hour, a further 50 ml of 2N NaOCH₃ solution are added. The mixture is then boiled under reflux for 3 hours. It is then evaporated to dryness, water is added and the organic phase is taken up in CH₂Cl₂. After evaporating, the residue is crystallised.

Yield: 58% of theory; melting point: 123° C. (from isopropanol).

The following were prepared analogously:

| Example No. | Formula | m.p. (°C.) | Yield, % of theory |
|---|---|---|---|
| | Ethyl 4-(5-(2-chloro-6-fluorophenyl)-2-pyrimidinyl)-1-piperazinecarboxylate | | |
| 55 | [2-chloro-6-fluorophenyl]-pyrimidinyl-piperazine-N—C(=O)—O—C₂H₅ | 106–107° | 46 |
| | Ethyl 4-(3,4-dimethoxyphenyl)-2-pyrimidinyl)-1-piperazinecarboxylate | | |
| 56 | H₃C—O, H₃C—O-phenyl-pyrimidinyl-piperazine-N—C(=O)—O—C₂H₅ | 165–166° (from ethanol) | 66 |
| | Ethyl 4-(5-(4-chlorophenyl)-2-pyrimidinyl)-1-piperazinecarboxylate | | |
| 57 | Cl-phenyl-pyrimidinyl-piperazine-N—C(=O)—O—C₂H₅ | 133–134° (from ethanol) | 60 |
| | Ethyl 4-(5-(3-indolyl)-2-pyrimidinyl)-1-piperazinecarboxylate | | |

| Example No. | Formula | m.p. (°C.) | Yield, % of theory |
|---|---|---|---|
| 58 | Ethyl 4-(5-(3-trifluorophenyl)-2-pyrimidinyl)-1-piperazinecarboxylate | 155–156° (from isopropanol) | 55 |
| 59 | | 123–124° | 55 |

EXAMPLE 60

Preparation of 1-(5-phenyl-2-pyrimidinyl)piperazine

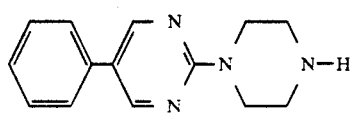

0.04 mol of ethyl 1-(5-phenyl-2-pyrimidinyl)-4-piperazinecarboxylate are boiled under reflux with 0.78 mol of KOH in 400 ml of $C_2H_5OH$ and 40 ml of $H_2O$ under $N_2$ protective gas for 15 hours. The mixture is evaporated to dryness, water is added and the residue is taken up in $CH_2Cl_2$. After washing with water, the organic phase is separated off and evaporated to dryness, whereupon the amine is obtained as crystals.

Yield: 90% of theory; melting point: 107°–108° C.

The following were prepared analogously:

| Example No. | Formula | m.p. (°C.) | Yield, % of theory |
|---|---|---|---|
| | 1-(5-(2-Fluoro-6-chlorophenyl)-2-pyrimidinyl)piperazine | | |
| 61 | | 87° | 79 |
| | 1-(5-(3,4-Dimethoxyphenyl)-2-pyrimidinyl)piperazine | | |
| 62 | | 140–141° (from ethyl acetate) dihydrochloride: 298–300° | 85 |
| | 1-(5-(4-Chlorophenyl)-2-pyrimidinyl)piperazine | | |
| 63 | | 157–158° (from ethanol) | 83 |
| | 1-(5-(3-Indolyl)-2-pyrimidinyl)piperazine | | |
| 64 | | 201–202° (from isopropanol) | 53 |
| | 1-(5-(3-Trifluorophenyl)-2-pyrimidinyl)piperazine | | |

| Example No. | Formula | m.p. (°C.) | Yield, % of theory |
|---|---|---|---|
| 65 | 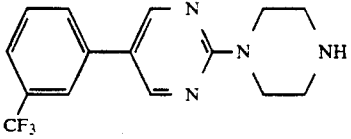 | 98–99° | 79 |

-continued

EXAMPLE 66

Preparation of 1-(5-iodo-2-pyrimidinyl)piperazine

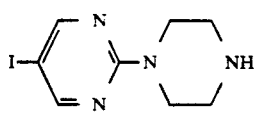

0.02 mol of 2-chloro-5-iodopyrimidine, 0.06 mol of piperazine and 100 ml of absolute dimethylformamide are heated to 100° for 45 minutes and then evaporated. The crystalline residue is shaken with potassium bicarbonate solution and methylene chloride. The substance contained in the methylene chloride phase is purified by column chromatography over silica gel 60. The amine obtained by elution with methylene chloride/methanol (7:3) is stirred with isopropyl ether and filtered off with suction.

Melting point = 135°–136° C.
Yield: 72% of theory.

The following was prepared analogously: 1-(5-Fluoro-2-pyrimidinyl)piperazine

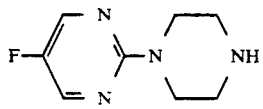

Melting point = 39°–40° C.,
Yield: 32% of theory.

EXAMPLE 68

Preparation of 2-(4-bromobutyl)-5-chloro-1,2-benzisothiazol-3(2H)one 1,1-dioxide

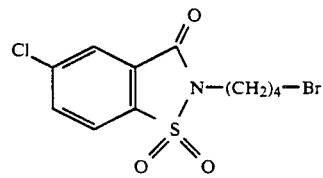

0.05 mol of 5-chloro-1,2-benzisothiazol-3(2H)one 1,1-dioxide is added to a suspension of 0.05 mol of NaH in 100 ml of DMF. Then 0.2 mol of 1,4-dibromobutane is added. The mixture is stirred at 100° C. for 1 hour. The mixture is evaporated and the residue is purified over silica gel 60, elution being carried out first with cyclohexane, then with methylene chloride/methanol (98:2).

Yield: 65% of theory; melting point: 72°–73° C. (from isopropanol).

The following were prepared analogously:

| Example No. | Formula | m.p. (°C.) | Yield, % of theory |
|---|---|---|---|
| | 2-(4-Bromobutyl)-6-chloro-1,2-benzisothiazol-3(2H)one 1,1-dioxide | | |
| 69 | 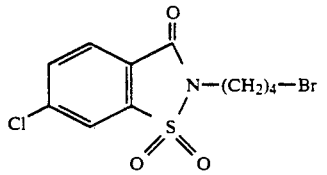 | 107° | 73 |
| | 2-(4-Bromobutyl)-5-fluoro-1,2-benzisothiazol-3(2H)one 1,1-dioxide | | |
| 70 | 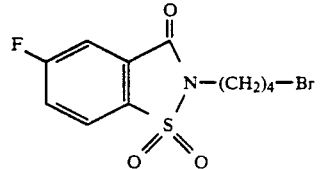 | 75° | 54 |
| | 2-(4-Bromobutyl)-6-fluoro-1,2-benzisothiazol-3(2H)one 1,1-dioxide | | |

| Example No. | Formula | m.p. (°C.) | Yield, % of theory |
|---|---|---|---|
| 71 | 2-(4-Bromobutyl)-6-fluoro... (4-F-benzisothiazol structure with N—(CH₂)₄—Br) | 72–73° | 78 |
| 72 | 2-(4-Bromobutyl)-6-nitro-1,2-benzisothiazol-3(2H)one 1,1-dioxide | 120–121° | 66 |
| 73 | 2-(4-Bromobutyl)-7-chloro-1,2,4-benzothiadiazin-3(4H)one 1,1-dioxide | 147.2° (from isopropyl ether) | 15 |

EXAMPLE 74

Preparation of 2-(4-(4-(2-pyrimidinyl)-1-piperazinyl)butyl)-6-amino-1,2-benzisothiazol-3(2H)one 1,1-dioxide

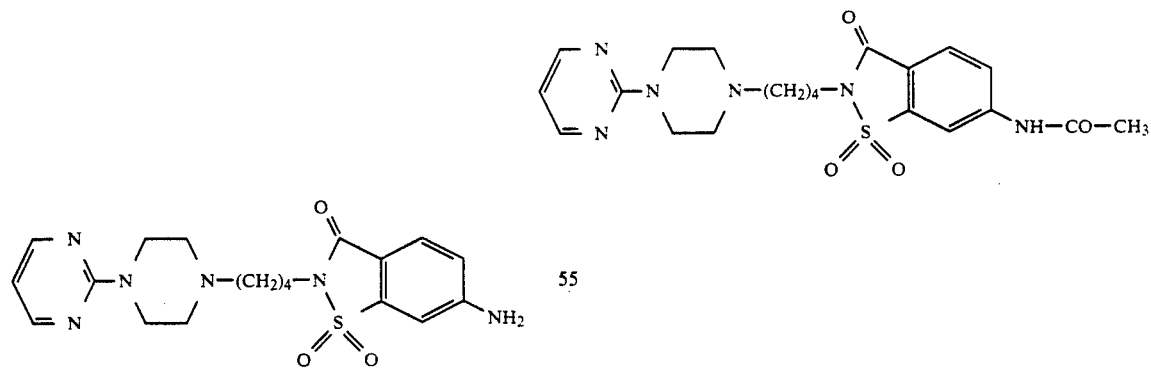

0.03 mol of 2-(4-(4-(2-pyrimidinyl)-1-piperazinyl)butyl-6-nitro-1,2-benzoisothiazol-3(2H)one 1,1-dioxide is dissolved in 50 ml of concentrated hydrochloric acid, and a solution of 0.13 mol of SnCl$_2$.2H$_2$O in 100 ml of concentrated hydrochloric acid is added. After the exothermic reaction is complete, the mixture is stirred for 30 minutes. The mixture is poured onto ice, filtered and the crystals are washed with water. After treatment with dilute sodium hydroxide solution, the base is extracted by shaking with methylene chloride, the solvent is evaporated off and the product is obtained as colourless crystals. Yield: 71% of theory; melting point: 150°–151° C.

EXAMPLE 75

Preparation of 2-(4-(4-(2-pyrimidinyl)-1-piperazinyl)butyl)-6-acetamido-1,2-benzisothiazol-3(2H)one 1,1-dioxide 200 ml of acetic anhydride are added to 0.06 mol of 2-(4-(4-(2-pyrimidinyl)-1-piperazinyl)butyl)-6-amino-1,2-benzoisothiazol-3(2H)one 1,1-dioxide, and the mixture is stirred at room temperature for 12 hours. It is then evaporated to dryness, isopropyl ether is added and the mixture is stirred for 1 hour. It is then filtered and the colourless crystals are dried in vacuo.

Yield: 91% of theory; melting point 162° C.

EXAMPLE 76

Preparation of 2-(4-(4-(2-pyrimidinyl)-1-piperazinyl)butyl)-6-ethoxycarbonylamino-1,2-benzisothiazol-3(2H)one 1,1-dioxide

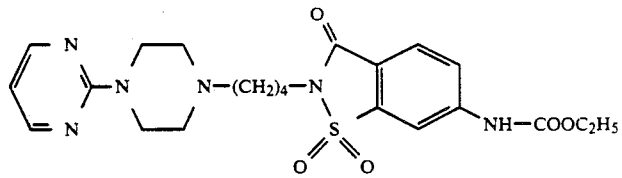

0.01 mol of 2-(4-(4-(2-pyrimidinyl)-1-piperazinyl)butyl)-6-amino-1,2-benzisothiazol-3(2H)one 1,1-dioxide is dissolved in 30 ml of absolute pyridine and, via cooling in ice, 0.02 mol of ethyl chloroformate is added. The mixture is then allowed to reach room temperature and is stirred for 12 hours. The solvent is evaporated off, ice-water is added and the mixture is extracted by shaking several times with methylene chloride. Colourless crystals are obtained after evaporating off the solvent.

Yield: 53% of theory; melting point 160° C.

EXAMPLE 77

Preparation of 2-(4-(4-(2-pyrimidinyl)-1-piperazinyl)butyl)-6-bis(methanesulphonyl)amino-1,2-benzisothiazol-3(2H)one 1,1-dioxide

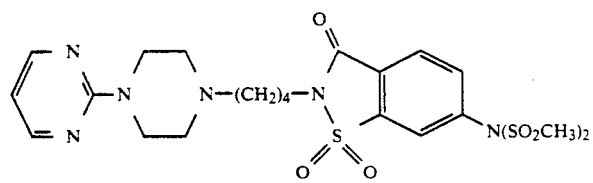

0.01 mol of 2-(4-(4-(2-pyrimidinyl)-1-piperazinyl)butyl)-6-amino-1,2-benzisothiazol-3(2H) 1,1-dioxide is dissolved in 50 ml of absolute pyridine and, via cooling in ice, 0.023 mol of methanesulphonyl chloride is added. The mixture is then allowed to reach room temperature and is stirred for 12 hours. The solvent is evaporated off, dilute sodium hydroxide solution is added and the mixture is extracted several times by shaking with methylene chloride. Purification is carried out by chromatography on silica gel eluting with $CH_2Cl_2/CH_3OH$ (10:1).

Yield: 23% of theory; melting point: 167° C. (decomposition).

EXAMPLE 78

Preparation of 2-(3-(4-(2-pyrimidinyl)-1-piperazinyl)propyl-5-fluoro-1,2-benzisothiazol-3(2H)one 1,1-dioxide 0.03 mol of 5-fluoro-2-(3-bromopropyl)-1,2-benzisothiazol-3(2H)one 1,1-dioxide and 0.03 mol of 1-(2-pyrimidinyl)piperazine are stirred at 50° to 60° C. with 0.03 mol of $K_2CO_3$ in 100 ml of absolute DMF for 2 hours. The mixture is then evaporated, water is added to the residue and the base is extracted with methylene chloride. Purification is carried out by chromatography on silica gel; the eluting agent is $CH_2Cl_2/CH_3OH$ (98:2), recrystallisation is on roluol.

Yield: 20% of theory; melting point: 117° to 118° C.

The following were prepared analogously:

| Example No. | Formula | m.p. (°C.) | Yield, % of theory |
|---|---|---|---|
| 79 | 2-(3-(4-(5-(4-Chlorophenyl)-2-pyrimidinyl)-1-piperazinyl)propyl)-1,2-benzisothiazol-3(2H)one 1,1-dioxide | 185° | 52 |
| 80 | 2-(2-(4-(5-(4-Chlorophenyl)-2-pyrimidinyl)-1-piperazinyl)ethyl)-1,2-benzisothiazol-3(2H)one 1,1-dioxide | 186° | 10 |

| Example No. | Formula | m.p. (°C.) | Yield, % of theory |
|---|---|---|---|

The following were prepared in analogy to Example 18:
2-(3-(4-(2-Pyrimidinyl)-1-piperazinyl)-2-hydroxypropyl)-1,2-benzisothiazol-3(2H)one 1,1-dioxide

| 81 | | 108° | 42 |

2-(3-(4-(5-(4-Chlorophenyl-2-pyrimidinyl)-1-piperazinyl)-2-hydroxypropyl)-1,2-benzisothiazol-3(2H)one 1,1-dioxide

| 82 | | 159° | 28 |

EXAMPLE 83

Preparation of 2-(4-(4-(2-pyrimidinyl)-1-piperazinyl)butyl)-1,3,2-benzodithiazole 1,1,3,3-tetroxide

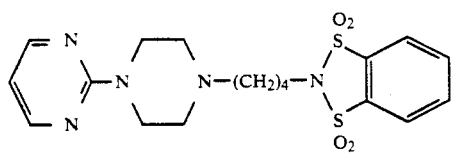

0.028 mol of 2-(4-bromobutyl)-1,3,2-benzodithiazole 1,1,3,3-tetroxide and 0.056 mol of 1-(2-pyrimidinyl)piperazine in 125 ml of absolute DMF are stirred at 25° C. for 6 hours. The mixture is then cooled to 0° C., 150 ml of water are added dropwise with stirring, and the substance which has crystallised out is filtered off with suction. The product is purified by chromatography on silica gel; the eluting agent is ethyl acetate.

Yield: 31% of theory; melting point: 178° C.

EXAMPLE 84

Preparation of 2-(4-bromobutyl)-1,3,2-benzodithiazole 1,1,3,3-tetroxide

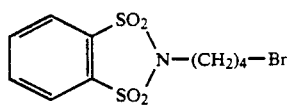

A solution of 0.65 mol of ammonia in 1,050 ml of absolute ethanol is added dropwise, with stirring, to 0.13 mol of 1,2-benzenedisulphonyl chloride in 720 ml of absolute toluene at 25° C. The mixture is stirred a further hour, slight cloudiness is removed by filtration through a layer of kieselguhr, and the filtrate is evaporated to dryness. The ammonium salt of 1,3,2-benzodithiazole 1,1,3,3-tetroxide is obtained.

Yield: 91% of theory; melting point: 246° to 247° C.

0.06 mol of the ammonium salt and 0.25 mol of 1,4-dibromobutane in 130 ml of absolute DMF are stirred at 130° to 140° C. for 5 hours. After cooling, the mixture is evaporated in a rotary evaporator and remaining 1,4-dibromobutane is removed by steam distillation. The reaction product is taken up in methylene chloride, purified by column chromatography on silica gel (eluting agent $CH_2Cl_2$/cyclohexane (7:3)) and finally recrystallised from isopropanol.

Yield: 35% of theory; melting point: 82° to 83° C.

EXAMPLE 85

Preparation of 2-(3-(4-(2-pyrimidinyl)-1-piperazinyl)-propyl)-7-methoxy-1,2,4-benzothiadiazin-3(4H)one 1,1-dioxide

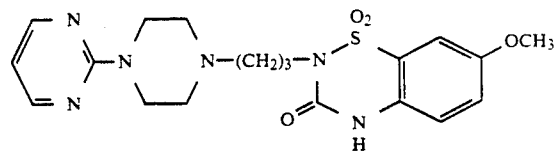

0.01 mol of 2-(3-bromopropyl)-7-methoxy-1,2,4-benzothiadiazin-3(4H)one 1,1-dioxide, 0.012 mol of 1-(2-pyrimidinyl)piperazine and 0.01 mol of triethylamine are dissolved in 30 ml of DMF and the solution is heated at 60° C., with stirring, for 1.5 hours. Then 15 ml of water are added and the reaction mixture is cooled to 0° C. The substance which crystallises out during this is filtered off with suction, stirred with isopropanol, again filtered off with suction and dried in vacuo. Yield: 53% of theory; melting point: 178° C.

The following were prepared analogously:

| Example No. | Formula | m.p. (°C.) | Yield, % of theory |
|---|---|---|---|

2-(3-(4-(2-Pyrimidinyl)-1-piperazinyl)propyl)-4-phenyl-1,2,4-benzothiadiazin-3(4H)one 1,1-dioxide -continued

| Example No. | Formula | m.p. (°C.) | Yield, % of theory |
|---|---|---|---|
| 86 | 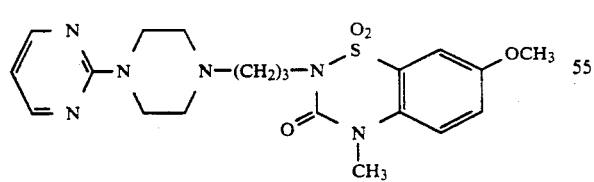 | 129° | 84 |

2-(4-(4-(2-Pyrimidinyl)-1-piperazinyl)butyl)-4-phenyl-1,2,4-benzothiadiazin-3(4H)one 1,1-dioxide

| 87 | | 227 | 76 |

2-(3-(4-(2-Pyrimidinyl)-1-piperazinyl)propyl)-7-chloro-1,2,4-benzothiadiazin-3(4H)one 1,1-dioxide

| 88 | | 208° | 55 |

EXAMPLE 89

Preparation of 2-(3-(4-(2-pyrimidinyl)-1-piperazinyl)propyl)-4-methyl-7-methoxy-1,2,4-benzothiadiazin-3(4H)one 1,1-dioxide of a total of 18 ml of water. It is purified by crystallisation from isopropanol.

Yield: 40% of theory; melting point: 146° C.

The following were prepared analogously:

| Example No. | Formula | m.p. (°C.) | Yield, % of theory |
|---|---|---|---|
| | 2-(3-(4-(2-Pyrimidinyl)-1-piperazinyl)propyl)-7-chloro-4-methyl-1,2,4-benzothiadiazin-3(4H)one 1,1-dioxide | | |
| 90 | | 128° | 72 |

0.028 mol of 2-(3-(4-(2-pyrimidinyl)-1-piperazinyl)propyl)-7-methoxy-1,2,4-benzothiadiazin-3(4H)one 1,1-dioxide is dissolved in 150 ml of absolute DMF, and 0.028 mol of sodium hydride is added to the solution and the mixture is stirred at room temperature for 0.25 hour. Then 0.028 mol of methyl iodide is added and the mixture is stirred at 25° C. for a further 2 hours. The product is precipitated as crystals by dropwise addition

EXAMPLE 91

Preparation of 2-(3-bromopropyl)-7-methoxy-1,2,4-benzothiadiazin-3(4H)one 1,1-dioxide

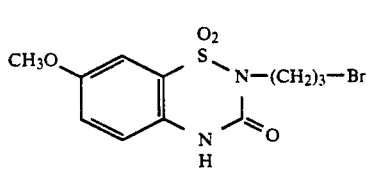

0.03 mol of 7-methoxy-1,2,4-benzothiadiazin-3(4H)one 1,1-dioxide is dissolved in 50 ml of absolute DMF, and 0.03 mol of sodium hydride is added. After 15 minutes, formation of the sodium salt was complete. Then 0.06 mol of 1,3-dibromopropane is added dropwise and the mixture is heated at 80° C. for 2 hours. The solvent is then distilled out and the residue is purified by column chromatography on silica gel. The eluting agent used was a mixture of CH$_2$Cl$_2$CH$_3$OH (98:2).

Yield: 46% of theory; melting point: 166° C.

The following were prepared analogously:

| Example No. | Formula | m.p. (°C.) | Yield, % of theory |
|---|---|---|---|
| | 2-(3-Bromopropyl)-4-phenyl-1,2,4-benzothiadiazin-3(4H)one 1,1-dioxide | | |
| 92 | 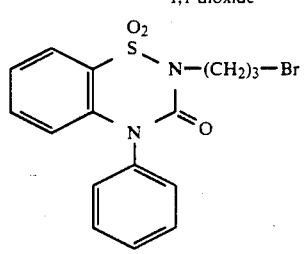 | 138° | 48 |
| | 2-(4-Bromobutyl)-4-phenyl-1,2,4-benzothiadiazin-3(4H)one 1,1-dioxide | | |
| 93 | 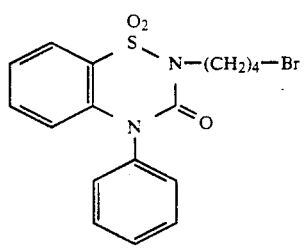 | 93° | 51 |

EXAMPLE 94

Preparation of N-(4-(4-(2-pyrimidinyl)-1-piperazinyl)butyl)-2-(acetylamino)benzenesulphonamide

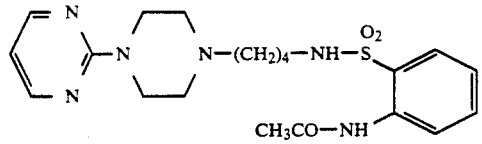

0.02 mol of N-(4-(4-(2-pyrimidinyl)-1-piperazinyl)-butyl)-2-aminobenzenesulphonamide and 0.5 mol of acetic anhydride are stirred at room temperature for 2 hours. The mixture is evaporated to dryness, concentrated aqueous ammonia solution is poured onto the residue and the base is extracted by shaking with methylene chloride. Purification is carried out by chromatography on silica gel; the eluting agent is CH$_2$Cl$_2$/CH$_3$OH (9:1). The substance is recrystallised from isopropanol.

Yield: 37% of theory; melting point: 99° C.

EXAMPLE 95

Preparation of N-acetyl-N-(4-(4-(2-pyrimidinyl)-1-piperazinyl)butyl)-2-(acetylamino)benzenesulphonamide

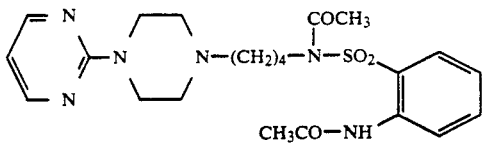

0.01 mol of N-(4-(4-(2-pyrimidinyl)-1-piperazinyl)-butyl)-2-aminobenzenesulphonamide is dissolved in 0.25 mol of acetic anhydride and the solution is heated at 100° C. for 3 hours. It is evaporated to dryness, concentrated aqueous ammonia solution is poured onto the residue and the base is extracted by shaking with methylene chloride. Purification is carried out by recrystallisation from isopropanol.

Yield: 47% of theory; melting point: 152° C.

EXAMPLE 96

Preparation of 1-(3-nitrophenyl)-3-(3-(4-(2-pyrimidinyl)-1-piperazinyl)-propyl)quinazoline-2,4(1H,3H)dione

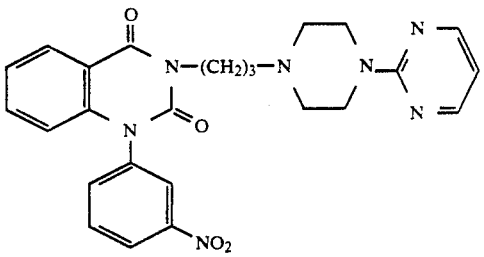

0.096 mol of 1-(3-aminopropyl)-4-(2-pyrimidinyl)piperazine is added to 0.0874 mol of 2-(3-nitrophenylamino)benzoyl chloride in 650 ml of dry dioxane and the mixture is heated under reflux for 1 hour. The crystals which separate out on cooling are filtered off, dissolved in water and potassium bicarbonate is added to the aqueous phase and this is extracted with dichloromethane. The organic phase is dried over sodium sulphate, evaporated and the dry residue is stirred with diisopropyl ether and petroleum ether.

Yield of substituted benzamide 44% of theory; melting point 101°–03° C.

0.0076 mol of the amide described above is suspended in 75 ml of dry tetrahydrofuran, 0.0152 mol of sodium hydride and, after evolution of hydrogen has ended, 0.0228 mol of carbonyldiimidazole are added, and the pasty reaction mixture is stirred at room temperature for 1 hour. The reaction mixture is hydrolysed by addition of water, the product is extracted with dichloromethane, and the residue remaining after evaporation of the solvent is recrystallised on dichloromethar/petroleum ether, and the crystalline product is dried at 70° C. in vacuo for 3 days.

Yield: 67.5% of theory, melting point 100°–115° C.

What is claimed is:
1. A piperazine derivative of the formula

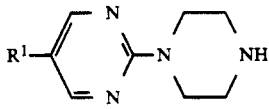

(II)

in which
R$^1$ represents, 4-methoxyphenyl, 4-chlorophenyl, 3-(trifluoromethyl)phenyl, 2-chloro-6-fluorophenyl or 3-indolyl.

* * * * *

UNITED STATES PATENT AND TRADEMARK OFFICE
CERTIFICATE OF CORRECTION

PATENT NO. : 5,187,276

DATED : February 16, 1993

INVENTOR(S) : Seidel et al.

It is certified that error appears in the above-identified patent and that said Letters Patent is hereby corrected as shown below:

Title Page    [75] Inventors:  6th inventor delete " Thurman" and substitute -- Schuurman --

Signed and Sealed this

Twenty-fourth Day of January, 1995

*Attest:*

BRUCE LEHMAN

*Attesting Officer*    *Commissioner of Patents and Trademarks*